(12) United States Patent
Boone, III et al.

(10) Patent No.: US 8,236,008 B2
(45) Date of Patent: Aug. 7, 2012

(54) MICRODERMABRASION TREATMENT HEADS

(75) Inventors: N. Brendon Boone, III, Encino, CA (US); Basil M. Hantash, East Palo Alto, CA (US); Kenneth B. Karasiuk, Oak Park, CA (US); Steven E. Wojcik, Mukilteo, WA (US)

(73) Assignee: Envy Medical, Inc., Westlake Village, CA (US)

( * ) Notice: Subject to any disclaimer, the term of this patent is extended or adjusted under 35 U.S.C. 154(b) by 640 days.

(21) Appl. No.: 12/040,867

(22) Filed: Feb. 29, 2008

(65) Prior Publication Data

US 2009/0222023 A1    Sep. 3, 2009

(51) Int. Cl.
*A61B 17/50* (2006.01)

(52) U.S. Cl. .................. 606/131; 451/359; 451/344

(58) Field of Classification Search .................. 606/131, 606/9, 133, 159, 187, 204.35, 215, 217, 216, 606/220, 225; D24/133, 147; 604/264; 451/359, 451/360, 102, 344, 449, 450
See application file for complete search history.

(56) References Cited

U.S. PATENT DOCUMENTS

| | | |
|---|---|---|
| 882,532 A | 3/1908 | McCall |
| 1,882,040 A | 10/1932 | Roehm |
| 1,898,652 A | 2/1933 | Williams |
| 2,228,676 A | 1/1941 | Renga |
| 2,266,931 A | 12/1941 | Wheeler |
| 2,338,339 A | 1/1944 | La Mere et al. |
| 2,608,032 A | 8/1952 | Garver |
| 2,655,146 A | 10/1953 | Force, Jr. |
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,085,573 A | 4/1963 | Meyer et al. |
| 3,236,231 A | 2/1966 | Schneider et al. |
| 3,476,112 A | 11/1969 | Elstein |
| 3,574,239 A | 4/1971 | Sollerud |
| 3,715,838 A | 2/1973 | Young et al. |
| 3,736,921 A | 6/1973 | Kawada |
| 3,818,904 A | 6/1974 | Kawada |
| 3,841,322 A | 10/1974 | Spelio |
| 3,841,323 A | 10/1974 | Stoughton |
| 3,964,212 A | 6/1976 | Karden |
| 4,003,373 A | 1/1977 | Spelio |
| 4,182,329 A | 1/1980 | Smit et al. |
| 4,216,233 A | 8/1980 | Stein |
| 4,241,499 A | 12/1980 | Perrone |
| 4,378,804 A | 4/1983 | Cortese, Jr. |
| 4,560,373 A | 12/1985 | Sugino et al. |
| 4,572,187 A | 2/1986 | Schetrumpf |
| 4,646,480 A | 3/1987 | Williams |

(Continued)

FOREIGN PATENT DOCUMENTS

DE        3421390        12/1985

(Continued)

*Primary Examiner* — S. Thomas Hughes
*Assistant Examiner* — Tin Nguyen
(74) *Attorney, Agent, or Firm* — Aka Chan LLP

(57) ABSTRACT

An abrasive tip is used to exfoliate skin and tissue through abrasive materials integrated in the tip. The tip also delivers fluid to the skin and vacuums the fluid and abraded tissue during treatment. Treated skin will look younger and healthier in appearance. In an implementation, the tip is replaceable and disposable.

23 Claims, 18 Drawing Sheets

U.S. PATENT DOCUMENTS

| | | |
|---|---|---|
| 4,676,749 A | 6/1987 | Mabille |
| 4,706,676 A | 11/1987 | Peck |
| 4,754,756 A | 7/1988 | Shelanski |
| 4,757,814 A | 7/1988 | Wang et al. |
| 4,836,192 A | 6/1989 | Abbate |
| 4,900,316 A | 2/1990 | Yamamoto |
| 4,917,086 A | 4/1990 | Feltovich et al. |
| 4,957,747 A | 9/1990 | Stiefel |
| 5,012,797 A | 5/1991 | Liang et al. |
| 5,037,431 A | 8/1991 | Summers et al. |
| 5,037,432 A | 8/1991 | Molinari |
| 5,100,412 A | 3/1992 | Rosso |
| 5,161,317 A * | 11/1992 | McDougall ............. 34/97 |
| 5,207,234 A | 5/1993 | Rosso |
| 5,377,701 A | 1/1995 | Fang |
| 5,699,810 A | 12/1997 | Pallikaris |
| 5,800,440 A | 9/1998 | Stead |
| 5,810,842 A | 9/1998 | Di Fiore et al. |
| 5,873,881 A | 2/1999 | McEwen et al. |
| 5,954,730 A | 9/1999 | Bernabei |
| 5,971,999 A | 10/1999 | Naldoni |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,120,512 A | 9/2000 | Bernabei |
| 6,136,008 A | 10/2000 | Becker et al. |
| 6,139,553 A | 10/2000 | Dotan |
| 6,139,554 A | 10/2000 | Karkar et al. |
| 6,149,634 A | 11/2000 | Bernabei |
| 6,162,232 A | 12/2000 | Shadduck |
| 6,196,982 B1 | 3/2001 | Ball |
| 6,241,739 B1 | 6/2001 | Waldron |
| 6,283,078 B1 | 9/2001 | Munetoki et al. |
| 6,299,620 B1 | 10/2001 | Shaddock et al. |
| 6,319,211 B1 | 11/2001 | Ito et al. |
| 6,387,103 B2 | 5/2002 | Shadduck |
| 6,423,078 B1 | 7/2002 | Bays et al. |
| 6,500,183 B1 * | 12/2002 | Waldron ............. 606/131 |
| 6,511,486 B2 | 1/2003 | Mercier et al. |
| 6,629,983 B1 | 10/2003 | Ignon |
| 6,641,591 B1 | 11/2003 | Shadduck |
| 6,942,649 B2 | 9/2005 | Ignon et al. |
| 2002/0016601 A1 * | 2/2002 | Shadduck ............. 606/131 |
| 2002/0107527 A1 | 8/2002 | Burres |
| 2004/0143274 A1 | 7/2004 | Shadduck |

FOREIGN PATENT DOCUMENTS

| | | |
|---|---|---|
| EP | 0258901 | 9/1988 |
| IT | 1184922 | 10/1987 |
| WO | 9923951 | 5/1999 |
| WO | 00/67692 | 11/2000 |
| WO | WO 2006002489 A1 * | 1/2006 |
| WO | WO 2007015729 A1 * | 2/2007 |

* cited by examiner

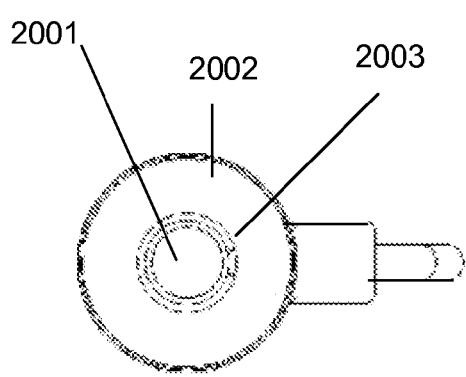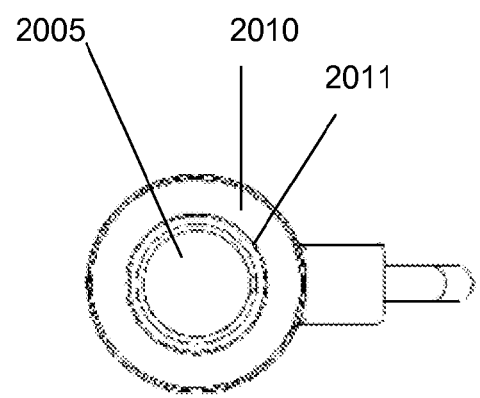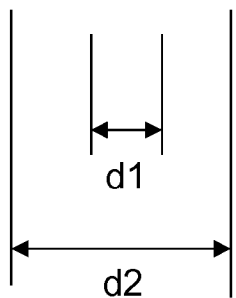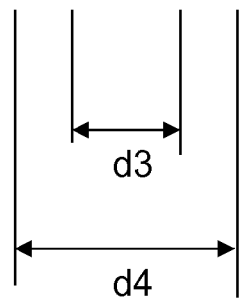
Figure 20A                Figure 20B

MICRODERMABRASION TREATMENT HEADS

BACKGROUND OF THE INVENTION

The invention relates to the field of devices to treat human skin and more specifically to an abrasive tip used to exfoliate skin and tissue through the use of abrasive materials, where this tip delivers fluid to the skin and vacuums the fluid and abraded tissue during treatment.

As people age, they looks for ways to maintain a youth appearance. Some invasive cosmetic techniques include surgical approaches including eye lifts, face lifts, skin grafts, and breast lifts. However, these invasive techniques also have risks and potential complications. Some people who have died during cosmetic surgery operations. Therefore, it is desirable to have noninvasive cosmetic techniques.

A noninvasive technique for obtaining a more youthful appearance is through microdermabrasion. Microdermabrasion is a process for removing dead cells from the outermost layer of the skin (the epidermis) to provide a younger and healthier looking appearance, remove wrinkles, clean out blocked pores, remove some types of undesirable skin conditions that can develop, and enhance skin tone.

The process of microdermabrasion must be performed with a certain degree of accuracy, so that underlying live layers of skin tissue are not removed or damaged, but that enough dead cells are removed to give effective results. Therefore, there is a need for improved system, devices, tips, and techniques for performing microdermabrasion.

BRIEF SUMMARY OF THE INVENTION

An abrasive tip is used to exfoliate skin and tissue through abrasive materials integrated in the tip. The tip also delivers fluid to the skin and vacuums the fluid and abraded tissue during treatment. In an implementation, the tip is replaceable and disposable.

The invention reduces the time period required for a microdermabrasion treatment. The invention simultaneously treats the skin with fluids, exfoliates the skin, and vacuums away the spent fluids, abraded skin particles, and other debris.

A wide variety of abrasive tips may be used with the invention. This may include, for example, different types of abrasive elements such as bristles, meshes, abrasive particles, or combinations of these. Many different sizes of tips are available. Thus, small skin surfaces such as the cheek, forehead, chin, and nose may be treated. Large surfaces such as the back, legs, or torso may also be treated.

In one embodiment, the fluids are directed to the perimeter of the abrasive tips. Thus, the skin to be exfoliated is surrounded with fluids. The skin is provided with a treatment of fluids before the microdermabrasion beings and a treatment of fluids after the microdermabrasion ends.

In an implementation, the invention is a device including: a tip having an abrading surface formed on a first side; a collar portion on a second side of the tip; a number of fluid channels formed on a second side of the tip, each channel extending through the collar through a first edge to a second edge of the tip, where the second edge of the tip is perpendicular to and touches the first side, and an angle between the first side and the first edge is less than ninety degrees; and at least one key notch, formed on the collar portion between two channel openings, where a surface of the collar is perpendicular to the first side. The fluid channels can conduct any fluid, including liquids or gases.

Further, in various specific implementations, the first side of the tip may have a circular shape. Each fluid channel is a groove formed in the first edge. There is a split in the collar portion at each point where a fluid channel passes through the collar. The fluid channels are evenly distributed about the second edge. An angle between the fluid channels is given by 360 degrees divided a total number of fluid channels (e.g., for four channels, the angle is 90 degrees; for three channels, the angle is 60 degrees; and for five channels, the angle is 72 degrees).

A first fluid channel has a first end at the first edge, a second fluid channel has a second end at the first edge, and the first and second ends are opposite of each other on the first edge. Then the ends of the fluids channels will be a maximum distance away from each other, while being on the first edge.

In a various specific implementations, the tip has four fluid channels. The abrading surface includes an abrasive disk connected to the first side (e.g., the abrasive disk can be abrasive paper like sandpaper glued to the abrading surface of the first side). The abrading surface includes of bristles connected to the first side. The abrading surface includes an abrasive mesh pad connected to the first side (e.g., the abrasive pad may be an exfoliating pad or sponge and made from a material such as nylon or natural fibers such as a loofah). The collar includes at least one key notch for each channel (e.g., for four channels, there are four key notches).

In an implementation, the invention is a device including: a tip having a number of bristles connected to a front surface on a first side; a fluid opening, surrounded by the bristles, on the first side, where the fluid opening extends to a second side, opposite to the first side; a first cylindrical side surface, connected to and perpendicular to the first side; and a number of prongs which extend away from the first cylindrical side surface and toward second side (e.g., the prongs may extend in a splay-like fashion from the tip).

Further, in various specific implementations, the tip includes a cylindrical column on the first side extending from the front surface away from the second side, where the fluid opening extends through the cylindrical column. The length of the cylindrical column is less than a length of the bristles. The cylindrical column may be about 50 percent (e.g., 40 to 60 percent) of a length of the bristles.

An implementation of the tip has at least three prongs. An implementation of the tip has at least four prongs. An angle between the prongs is given by 360 degrees divided a total number of prongs (e.g., for four prongs, the angle is 90 degrees; for three prongs, the angle is 60 degrees; and for five prongs, the angle is 72 degrees). Further, in an implantation, a first prong extends from a first position on the first cylindrical side surface, a second prong extends from a second position on the first cylindrical side surface, and the first and second positions are opposite of each other (i.e., 180 degrees apart) on the first cylindrical side surface.

In various specific implementations, the prongs touch the front surface. When the prongs touch the front surface, there are three prongs. The bristles may be arranged in any number of groupings (e.g., an even number of groupings, an odd number of groupings, four groupings, five groupings, and six groupings).

In an embodiment, there is a second cylindrical side surface, concentric with the first cylindrical side surface and having a smaller circular cross-sectional area. This second cylindrical side surface is connected to the first cylindrical side surface through a step-down ring. When the tip has a second cylindrical side surface, there are four prongs. When there are four prongs, there are six groupings of bristles.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 20A shows a front view of a first implementation of an abrasive tip having a six millimeter diameter and tip holder.

FIG. 20B shows a front view of a second implementation of an abrasive tip having a nine millimeter diameter and tip holder.

DETAILED DESCRIPTION OF THE INVENTION

This patent application incorporates by reference U.S. patent application Ser. No. 10/393,682, filed Mar. 19, 2003; U.S. Pat. No. 6,695,853, filed Nov. 21, 2001, and issued Feb. 24, 2004; and U.S. provisional patent application Ser. No. 10/393,682, filed Mar. 19, 2003.

Figure 1:
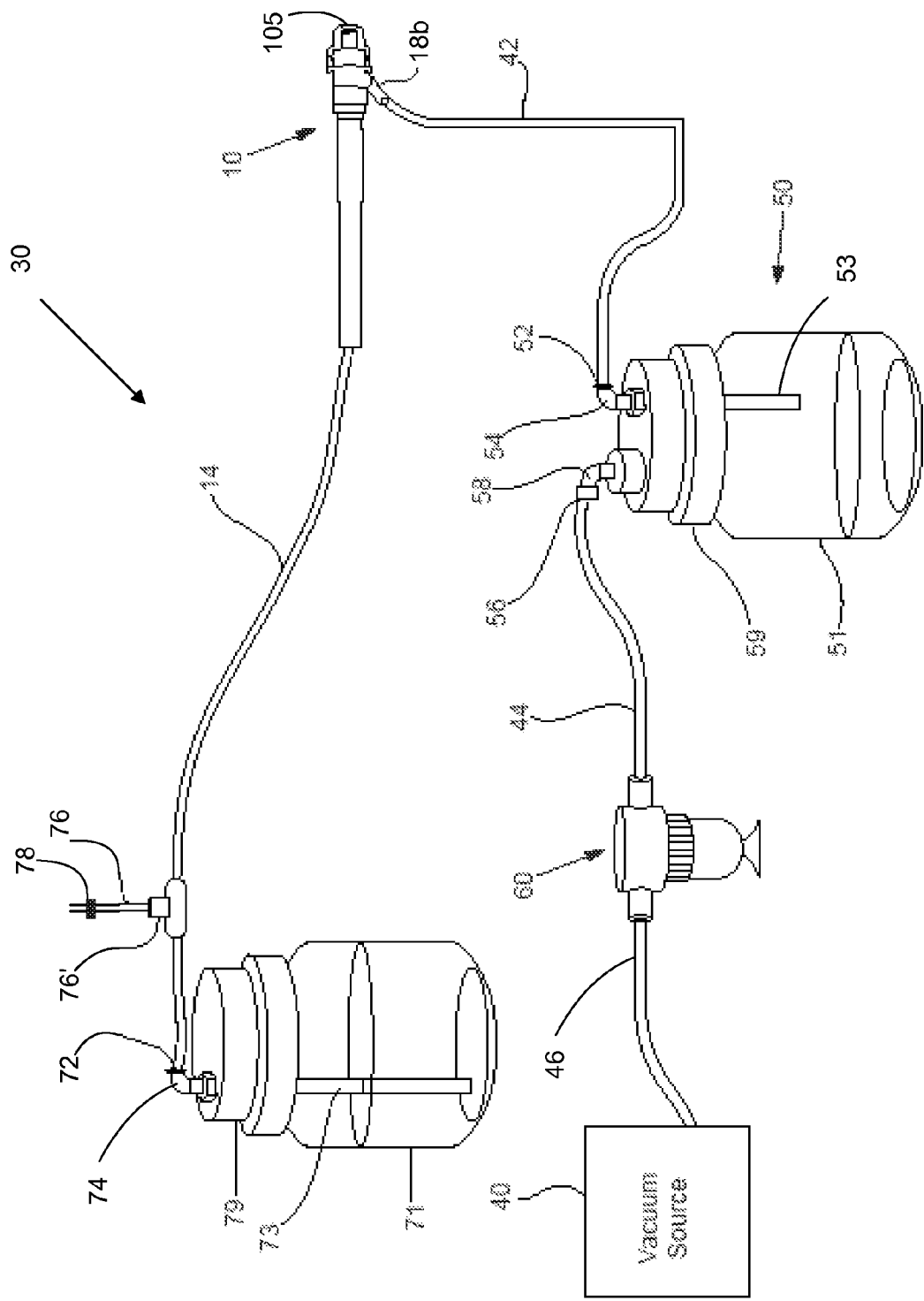
FIG. 1 shows a microdermabrasion system according to the present invention.

FIG. 1 shows an example of a microdermabrasion or dermabrasion system 30 according to the present invention, which incorporates a wand 10. A vacuum opening 18b is connected with a vacuum source 40 as described above, by a vacuum line 42. A collection reservoir 51 and, optionally, an inline filter 60 are connected in the vacuum line 42 between wand 10 and vacuum source 40. Vacuum line 42 connects to an input 52 to a collection reservoir 50 via an elbow 54, for example, and an output 56 connects with a second vacuum line 44 via an elbow 58, for example. A manifold cover 59 seals the input (52, 54) and output (56, 58) connections with the collection reservoir 51 which is typically a jar made of glass or plastic for example. An extension tube 53 connects with input 52, 54 and extends into the collection reservoir 51 to ensure effective delivery of waste materials (abraded skin particles and, optionally, fluids) to collection reservoir 51.

Optionally, a back-up filter 60 may be provided in-line between the vacuum line 44 and a vacuum line 46 as added insurance that no or substantially no fluid, skin particles, abrasive particle or other materials being collected by collection reservoir 51 can be transported to vacuum source 40. Filter 60 may be an in-line condensation filter, such as water condenser produced by Wilkerson Labs and available as part no. F0001-000 from Nor-Cal Controls, Incorporated of San Jose, Calif.

The vacuum source 40 may be the same as that provided for currently existing microdermabrasion devices, such as the ProPeel, MDPeel or iPeel, for example, each available from Emed, Incorporated of Westlake Village, Calif. A power switch is used to activate the vacuum source 40 and a vacuum in the range of about 2 pounds per square inch to about 14 pounds per square inch is generally used during a procedure, depending upon the skin condition of the person being treated.

Tube 14 extends from the microdermabrasion wand 10, and connects with an output 72 of a fluid reservoir 71 via an elbow 74, for example. A breather line 76 may be connected inline via a T-joint 76', for example, or other interconnection, and includes an adjustable valve 78 or other means for varying an amount of air that is allowed into the tube 14. This feature not only allows the amount of vacuum to be adjusted for a given fluid, but allows fluids having different viscosities to be applied at the same vacuum level, since different viscosities will require varying amounts of air to be introduced into the breather line 76, to give a constant vacuum level.

Alternatively, a breather line or input with adjustment valve may be located on elbow 74 or directly on a manifold cover 79. Still further, a valve or other flow control mechanism may be provided in the fluid delivery line 14 to control the amount of liquid passing through the line. This feature can be provided alternatively, or in addition to the breather line discussed above.

An input may be provided in manifold cover 79 which may be open to the atmosphere to prevent vacuum buildup in fluid reservoir 71. Manifold cover 79 seals the output (72, 74) connections with fluid reservoir 71 which is typically a jar made of glass or plastic, for example, and contains lotions, vitamins, other skin treatment fluids, or combinations of these to be applied to the skin by wand 10. An extension tube 73 connects with output 72, 74 and extends into the fluid reservoir 71 to near the bottom of the fluid reservoir to ensure that most all of the contents of fluid reservoir 71 are capable of being delivered through the system.

Abrasive particles, such as corundum crystals, sodium bicarbonate particles or other abrasive particles, including those discussed in U.S. Pat. No. 5,971,999 (which is incorporated by reference), for example may be included in fluid reservoir 71 for delivery through the system to perform a microdermabrading function. However, in the present invention, microdermabrasion is typically accomplished via a bristled tip 105, abrasive tip, or both. If used, the abrasive particles may be used together with any of the fluids mentioned above, with some other fluid carrier medium, such as those described in U.S. Pat. No. 5,971,999, for example, or both.

Fluid reservoir 71 may contain solution or a suspension for purposes other than abrasion or pure abrasiveness. The compositions used in the present invention can include a wide and diverse range of components. The *International Cosmetic Ingredient Dictionary and Handbook*, 12$^{th}$ edition, 2008, which is incorporated by reference, describes an extensive variety of cosmetic and pharmaceutical ingredients commonly used in the skin care industry, which are suitable for use in the compositions of the present invention.

General examples, types or categories, or both, of compounds that may be employed include: beaching formulations (e.g., 2 percent to 4 percent hydroquinone, 2 percent Kojic Acid, 1 percent Vitamin K, and 1 percent Hydrocortisone in an aqueous base); acne treatment formulations (e.g., Salycilic Acid, alcohol base buffered by witch hazel, etc.); fine lines/wrinkle treatment formulations (e.g., Hyaluronic acid is an aqueous base); hydrating formulations (e.g., Calendula, vitamins A, D, E, or other vitamins, or combinations of these in a mineral oil base); antioxidant formulations; free radical scavengers (e.g., vitamins A, E, K, or other vitamins, or combinations of these in a mineral oil base); pH adjusters; sunscreen agents; tanning agents and accelerators; nonsteroidal anti-inflammatory actives (NSAIDS); antimicrobial and antifungal agents; moisturizers; lightening agents; humectants; numbing agents; and water, or combinations of these.

The solution or suspension may contain extracts such as those from plants, vegetables, trees, herbs, flowers, nuts, fruits, animals, or other organisms, or combinations of these. Such extracts may be used to help condition the skin, provide a relaxing aroma, or both.

The solution or suspension may also contain viscosity increasing or decreasing agents, colorants, or combinations of these. In a specific implementation of the invention, the viscosity of the fluids used is about 1 centipoise (e.g., about 0.5 to 1.5 centipoise). However, in other implementations, the viscosity may range from 1 centipoise to 100 centipoise. The viscosity may be, for example, 0.2, 0.3, 0.4, 0.5, 0.6, 0.7, 0.8, 0.9, 1.1, 1.2, 1.3, 1.4, 1.5, 1.6, 10, 20, 30, 40, 50, 60, 70, 80, 90, or more than 100 centipoise. In other applications the viscosity may be less than 1 centipoise.

In a specific implementation, the fluids, abrasive particles, or both for fluid reservoir 71 may be packaged as a concentrated solution, powder, solids, or combinations of these to be mixed, diluted, or both by the microdermabrasion system 30.

Other examples of product categories that may be employed alone or in combination with other compounds include, antiseptics, astringents, cleansers, pore decongestants, balms, botanicals, collagen stimulators, herbs, microemulsifiers, oxygen delivery vehicles, proteins, serums, skin firming agents, toners, topical anesthetics, emulsions, ointments, gels, tyrosinase inhibitors, and other related product categories.

Individually named products that may be used (with associated benefit indicated parenthetically) include: Aloe Vera (calming); alpha hydroxy acids (peel); alphalipoic acid (antioxidant); benzoil and other peroxides (acne); ceramide (hydrator); copper (toning); copper peptide (toning); CoQ-10 (coenzyme Q-10) and other enzymes (toning); cortisone (calming); glycolic acids (peel); hyaluronic acid (collagen stimulation); hydrolipids (hydrator); hydroquinones (bleaching); lactic acids (peel); magnesium ascorbic phosphate (free radical scavenger, collagen stimulator, bleaching); niacin (vascular dilation); phospholipids (moisturization); potassium (toning, psoriasis), and salycilic acids (acne); and related products. Of course, any combination of such elements may be provided-even in connection with abrasive particles.

Any of the products listed may be used with the microdermabrasion treatment tips of the invention. For example, the groves of a tip which may be used to conduct botanicals, Aloe Vera, or alpha hydroxy, to name a few examples, to a patient's skin. The channels through which fluid is delivered may be partially formed in a tip and partially formed in a tip holder. When the tip and tip holder are put together, the groves in each of these mate to form a complete channel opening.

As another example, coenzyme Q-10, glycolic acids, or vitamin E, to name a few example, may be conducted through an opening, surrounded by bristles, to the skin of a patient. The opening may extend to a position closer to patient's skin through a cylindrical column, nipple, or other structure to achieve a similar purpose.

Note, however, the present system may be used by eliminating the fluid reservoir 71 altogether, where microdermabrasion is performed in a "dry state" and tube 14 is simply left open to atmosphere, with or without a filter or valve, or both, for adjusting the amount or flow rate of air that is allowed into tube 14. Similarly, dry or externally lubricated vacuum massage of tissue may be accomplished by a tip having a smooth surface.

Figure 2:
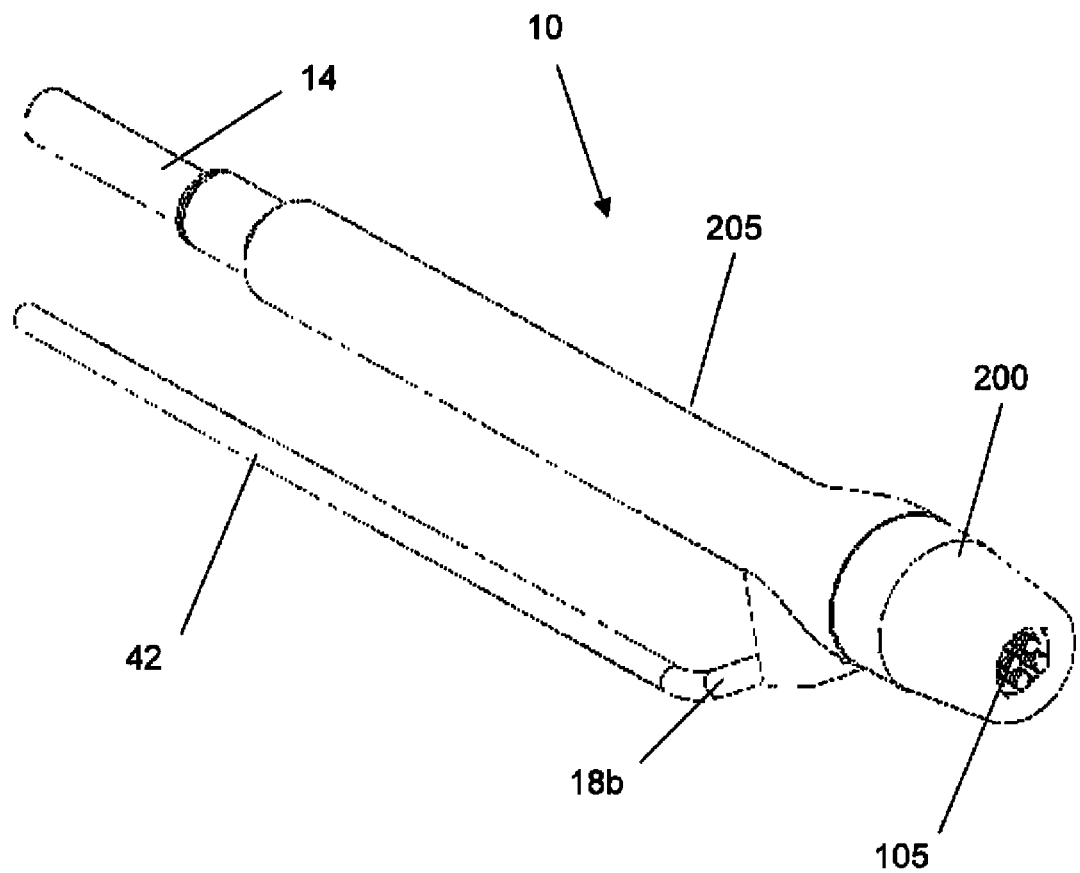
FIG. 2 shows a wand of the present invention.

FIG. 2 shows a wand 10 in a specific implementation of the present invention. To perform microdermabrasion, a user holds the wand in the user's hand and applies the tip to a patient. The wand has an elongated handle 205 which facilitate grasping by a user. The wand 10 includes a tip holder 200 which, in a specific implementation, holds a bristled tip 105. In other implementations, other types of tips may be used including, for example, tips with abrasive particles, abrasive disks, and tips with smooth surfaces.

Tube 14 is connected to an end of the wand 10. Tube 14 delivers the fluids to the wand 10. The fluids flow through the wand 10. The fluids exit the bristled tip 105, the tip holder 200, contact the skin, and the flow back into wand 10 and through vacuum line 42 which connects to a port 18*b*.

There are numerous technique on how a user can apply the wand and tip to perform microdermabrasion. For example, one approach is draw the tip across the skin of the patient in a single direction, generally away from the center or nose of the patient's face (when working on the patient's face). Another approach is to use a scrubbing motion, moving the tip back and forth on the face.

One of ordinary skill in the art will appreciate that many different shapes and materials may be employed for the handle 205 and the present invention is not to be limited to an elongated, substantially cylindrical handle 205 as shown. In the example of FIG. 2, handle 205 is made of plastic, such as nylon or other plastic having sufficient toughness and mechanical strength, but may also be made of metal, such as stainless steel or aluminum, for example, or ceramics or composites such as carbon fiber. The handle may include a combination of materials. For example, a rubber sleeve may be placed over handle 205 which may be made of plastic. The rubber sleeve provides a secure surface for a user to grasp. The surface of the handle may also be textured, knurled, or both in order to provide a slip-resistant surface.

Tube 14 may be flexible and may be made of polyvinyl chloride (PVC) or other compatible plastic or polymer, for example. Similarly, all other vacuum lines (e.g., vacuum line 42) described herein are flexible to afford maneuverability to wand 10 and may be made of PVC or other compatible plastic.

Figure 3:
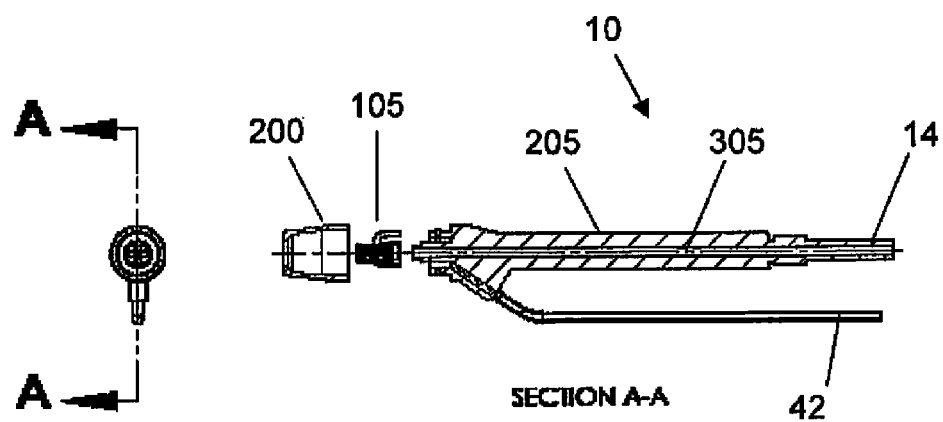
FIG. 3 shows a cross-sectional view of the wand with a tip holder, bristled tip, and handle.

FIG. 3 shows an exploded view of wand 10. A user may assemble or disassemble the wand by placing abrasive tip 105 onto the front of the wand 10 followed by tip holder 200. In an implementation, the user can easily replace parts of the wand as needed. Because the wand's design incorporates replaceable and easy to remove and assemble parts, users are able to do their own maintenance and repair.

Handle 205 is annular or tubular, providing a passageway 305 for fluids in tube 14 to pass through. Fluid flows through passage way 305, bristled tip 105, and tip holder 200 where the fluids contact the skin. The fluids then flow back into the wand 10 and through vacuum line 42.

Figure 4:
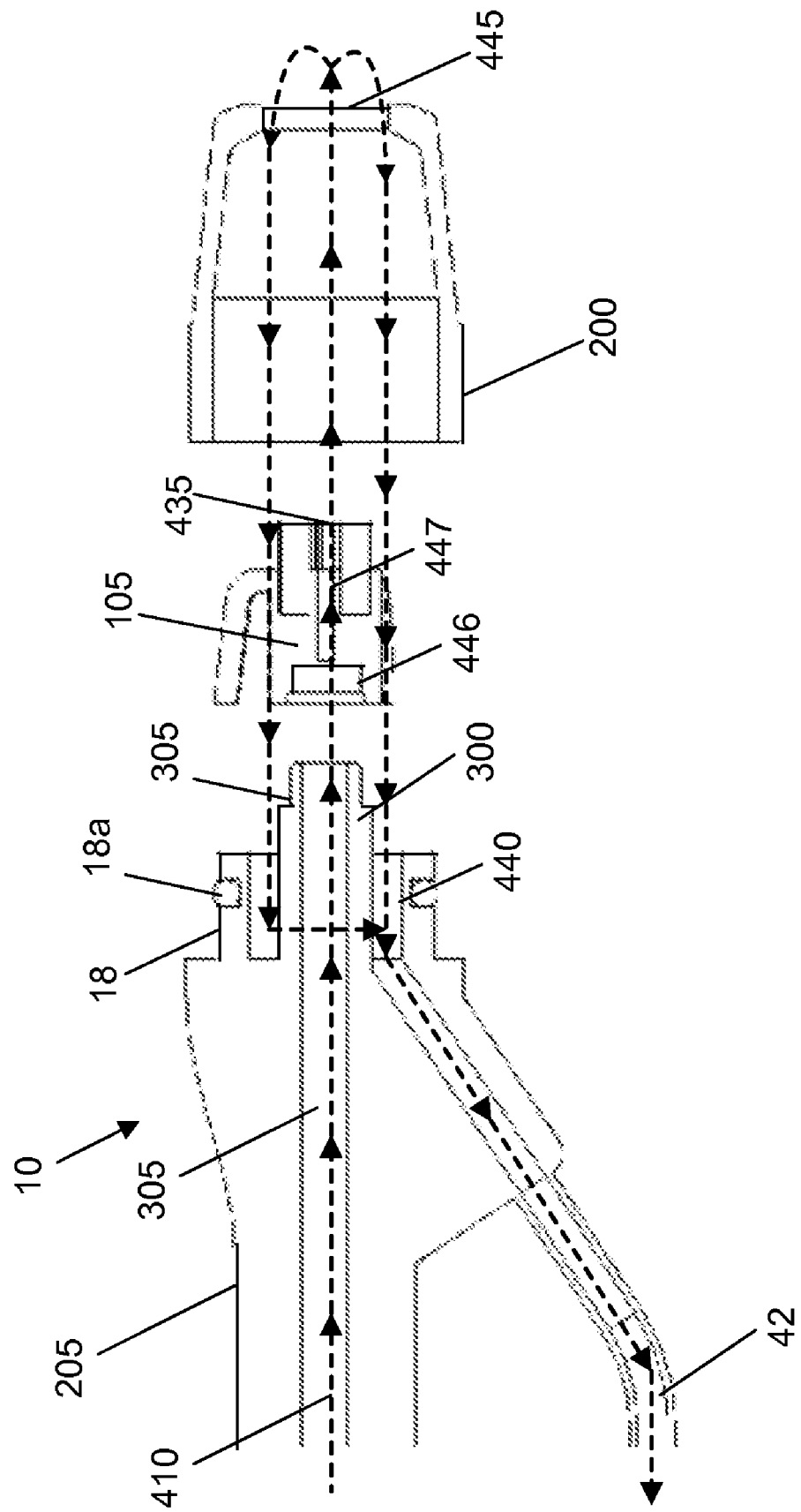
FIG. 4 shows cross-sectional view of the wand and a vacuum loop flow path.

FIG. 4 shows a cross-sectional view of wand 10. A vacuum loop 410 shows the flow of fluids. For use in microdermabrasion, wand 10 is positioned such that tip holder 200 contacts the skin surface to be microabraded. Vacuum source 40 (see FIG. 1) is turned on to establish a vacuum within the system. The order of positioning and turning on the vacuum source 40 is not critical as the vacuum source 40 can be turned on prior to contacting the tip holder 200 to the skin. The vacuum loop 410 will not be closed until such time that an opening 445 on the tip holder 200 is sealed by the skin.

With reference to FIG. 1 and FIG. 4, when vacuum source 40 is turned on a targeted area of the skin is drawn up into opening 445 and a central portion of the targeted area of skin is drawn into contact with bristled tip 105. At the same time, fluids in fluid reservoir 71 are drawn through tube 14 and into wand 10. The fluids follow vacuum loop 410 through passageway 305, through bristled tip 105, through an opening 435 on the bristled tip 105 and finally out opening 445 where the fluids treat the skin.

The fluids then reenter opening 445 and pass through a vacuum created in an annular space 440. Vacuum loop 410 now carries with it the exfoliated skin particles and any other waste that was removed through the microdermabrasion process. The fluids travel within vacuum line 42 and are collected in the collection reservoir 51. Since annulus 440 surrounds both the bristled tip 105 and opening 435, there is little to no spent fluid or debris that must later be cleaned from the skin.

This application describes a specific implementation of the invention, where the flow direction is as shown in FIG. 4: the fluid is delivered through a passageway in the wand to the tip. This fluid may then vacuumed into the vacuum line. However, an alternate embodiment of the invention, the flow direction is opposite of that shown in FIG. 4, where fluid is drawn into the central passageway of the wand from line 42.

As the user of the wand 10 glides the tip holder 200 over the skin, bristled tip 105 is scraped over the skin wherein microdermabrasion of that portion of the skin is performed.

A male to female connection between the bristled tip 105 and the handle 205 acts as a helpful guide to properly position the bristled tip to the handle. Bristled tip 105 includes a cavity 446. In a specific implementation, cavity 446 forms a female core which fits onto a distal end 305 of a cannula 300. That is distal end 305 forms a male core which fits into cavity 446. Bristled tip 105 fits onto distal end 305 using, for example, an interference or press fit. However, in other implementations, other attachment mechanisms may be used. For example, bristled tip 105 may include a tab to create a snap fit between the bristled tip 105 and the cannula 300. As another example, bristled tip 105 may thread onto cannula 300.

In other implementations, distal end 305 may form a female core. Bristled tip 105 may then include a male protrusion that fits into the female core of distal end 305.

Bristled tip 105 also includes a cavity 447. Cavity 447 is coupled to the opening 435 at one end of the bristled tip 105 and cavity 446 at the opposite end of bristled tip 105. This allows fluids to pass through bristled tip 105 using cavity 446, cavity 447, and eventually exiting at opening 435.

Tip holder 200 fits over bristled tip 105 and onto vacuum head base 18. One or more O-rings 18a or other sealing members (e.g., gasket) may be provided between vacuum head base 18 and tip holder 200 to facilitate the pressure tight seal. Tip holder 200 may be friction fit, provided with threads, or both, or another attachment means may provide a pressure tight fit between the components. For example, a snap fit such as an annular snap fit may be used. Alternatively, the tip holder 200 may be integrally machined or molded with vacuum head base 18. In another implementation, bristled tip 105 may be integrally machined or molded with tip holder 200.

Figure 5:
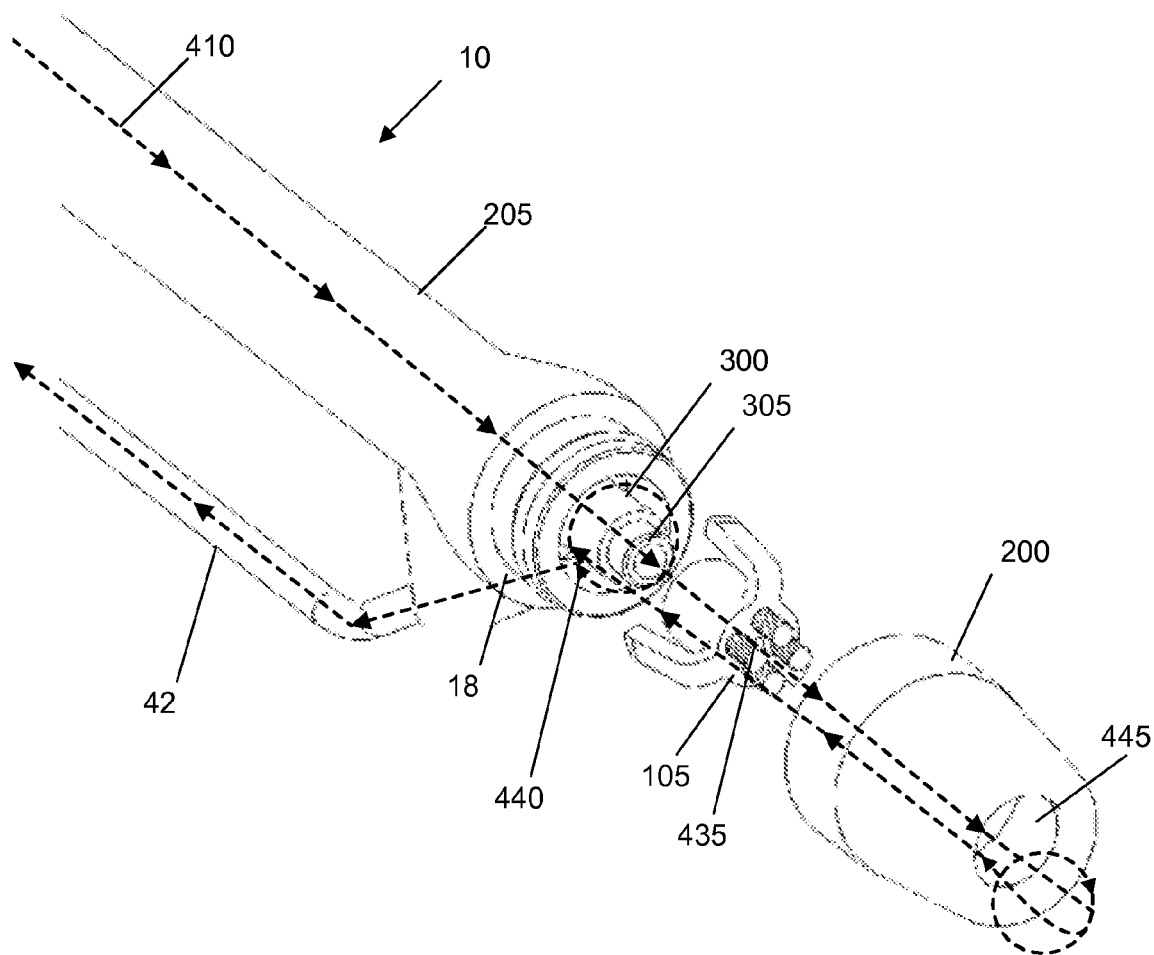
FIG. 5 shows a perspective view of the wand and the vacuum loop flow path.

FIG. 5 shows a perspective view of the vacuum loop 410. When vacuum source 40 (see FIG. 1) is turned on, fluids are pulled through handle 205 and cannula 300. The fluids continue through distal end 305 of the cannula where the fluids pass through bristled tip 105 and exit at an opening 435 on the bristled tip 105. The fluids exit tip holder 200 at an opening 445 and treat the skin. A vacuum created in annular space 440 pulls the fluids back into the tip holder 200 where the fluids move past the outside of bristled tip 105. The fluids are pulled into vacuum line 42 and are collected in collection reservoir 51 (see FIG. 1).

Figure 6:
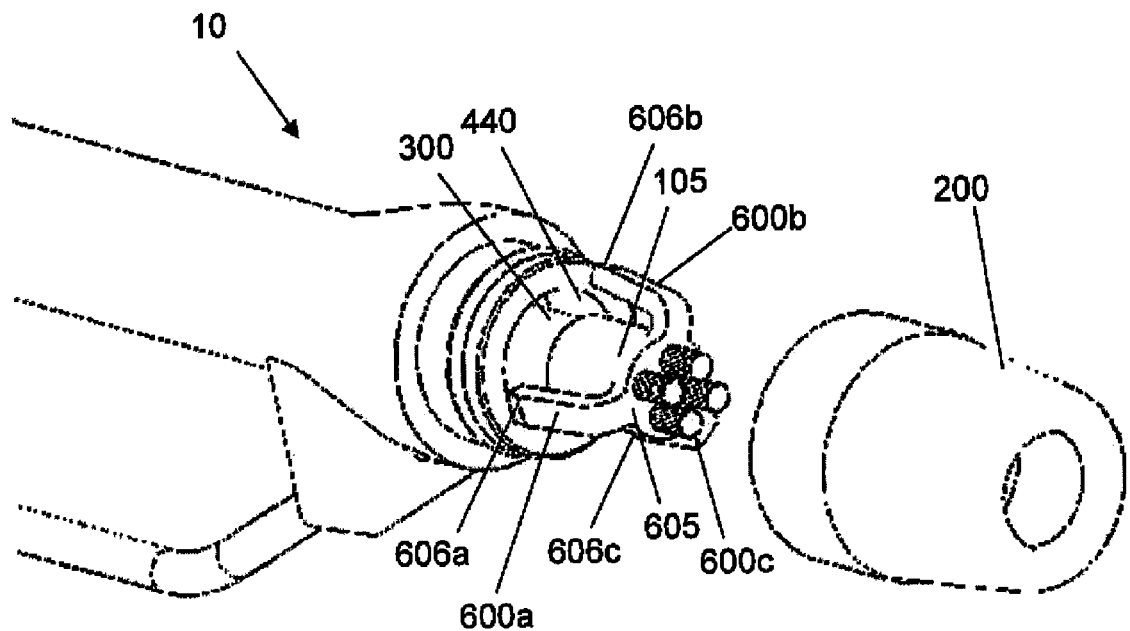
FIG. 6 shows a perspective view of a first implementation of the bristled tip placed on the handle.

FIG. 6 shows a perspective of bristled tip 105 placed onto cannula 300. In a specific implementation, the bristled tip 105 includes support ribs 600a, 600b, and 600c. When tip holder 200 is fitted over the bristled tip, the support ribs connect with the inner surface of the tip holder. The support ribs help to support and stabilize the bristled tip 105 in tip holder 200. The support ribs help to ensure that the bristled tip 105 is properly aligned in the holder. Fluid can flow through the tip, treat the skin, and be vacuumed back into the tip holder.

In a specific implementation, support ribs 600a, 600b, 600c are attached such that they are initially flush with a front face 605 of the bristled tip 105. However, in other implementations, the support ribs may be attached such that they are offset from the front face 605 of the bristled tip 105 (see, e.g., FIG. 9). Support ribs 600a, 600b, 600c extend outwardly and then turn to extend longitudinally down the length of the bristled tip 105 and at an angle such that their tips 606a, 606b, and 606c are splayed. The angle may match the interior surface angle of the tip holder 200. This allows support ribs 600a, 600b, 600c to contact the inner surface of the tip holder 200 for support and stabilization.

When the tip and tip holder are assembled together, support ribs 600a, 600b, and 600c touch an inside surface of the tip holder and help form annular space 440. Specifically, the annular space is formed between the inner surface of the tip holder and exterior surface of bristled tip 105. Generally, the less volume or space taken up by the ribs enlarges the volume of the annular space.

In a specific implementation, fluids and abraded tissues are vacuumed back into the wand through the annular space. This annular space creates an annular vacuum region that surrounds the passageway of the wand where fluids flow to the tip. The volume of the annular space may vary depending on the specific design, but generally, larger volume annular spaces will help prevent potential blockage or other similar problems, especially when compared to pores or other structures that will restrict flow more.

The support ribs also help to ensure that the bristled tip 105 is properly aligned so that fluid can flow through, treat the skin, and be pulled back into the tip holder.

In a specific implementation, support ribs 600*a*, 600*b*, 600*c* are positioned at equal distances from each other around the bristled tip 105. For example, the support ribs may be placed at 60 degree angles from each other as shown. However, in other cases, the support ribs may not be equally positioned in relation to each other. It should be appreciated that any arrangement or number of support ribs (including no support ribs) is possible so long as the fluids are able to pass from the front of the tip holder 200 to the back of the tip holder 200.

Consequently, a flange, or a portion of a flange may be used between the bristled tip 105 and the tip holder 200 either with or without one or more support ribs. For example, where a flange completely encircles the bristled tip 105, the flange may contain one or more openings which allow fluids to pass from the front of the tip holder 200 to the back of the tip holder 200.

In a specific implementation, there may be a total of three support ribs as shown in FIG. 6. However, in other implementations there may, for example, be four support ribs. In yet another implementation, there may be no support ribs, one, two, five, or more than five support ribs.

In a specific implementation, tips 606*a*, 606*b*, and 606*c* of the support ribs may have beveled edges. These beveled edges allow the tip holder 200 to easily slide on and off over the bristled tip 105.

In a specific implementation, the support ribs 600*a*, 600*b*, 600*c* are molded or machined as an integral part of the bristled tip 105 as shown. In other implementations, the support ribs are molded or machined as an integral part of the tip holder 200. For example, the interior surface of tip holder 200 may contain one or more protruding support ribs that contact bristled tip 105 when tip holder 200 if placed over bristled tip 105. In yet another implementation, there may be a combination of support ribs which may be molded or machined as an integral part of the tip holder 200 and bristled tip 105.

The tip holder 200 is smooth surfaced and adapted to glide over the skin as fluids (e.g., lotions, conditioners, vitamins, oils) exit the wand 10 to treat the skin. Tip holder 200 and treatment head 105 may, for example, be impregnated with polytetrafluoroethylene (PTFE), treated with wax, or include other hydrophobic ingredients to ensure that fluids do not adhere to tip holder 200 and treatment head 105.

The tip holder 200 and treatment head 105 may be made of metal (e.g., stainless steel, aluminum, titanium, brass) or plastic such as nylon, thermoplastics, polyethylene, polycarbonate, acrylonitrile butadiene styrene (ABS), or Delrin. Glass, such as Pyrex, for example, may also be used. Tip holder 200 may be, although not necessarily, transparent or translucent. A transparent tip holder may allow better visualization by the operator during use.

The treatment tip and tip holder of the invention (in the various embodiments described and shown in this application) are designed to be removable and installable by the user. Further, the user can dispose of used or old tips or holders, or both, and easily replace them with new (or clean) ones. Also, the user can remove the tips to clean them or clean the passages to ensure the flow, vacuum and fluid, are clear, so that the microdermabrasion device will be operating at full efficiency. Also, in an embodiment, the tip and tip holder are designed to be low cost (e.g., made of less expensive materials) and disposable.

The design may be such that the tip wears faster than the tip holder. So users may stock up with greater numbers of replacement tips than holders. When a tip wears out, the user replaces the tip without needing to replace the holder. This is analogous to the situation of replacing an ink refill insert of a pen. For example, the holder may be replaced once for every seven (or other number) of tips. This lowers the cost of use for users, because the tip, which needs more frequent replacement because it is subject to more wear and tear, is replaceable separately from the tip holder.

Figure 7:
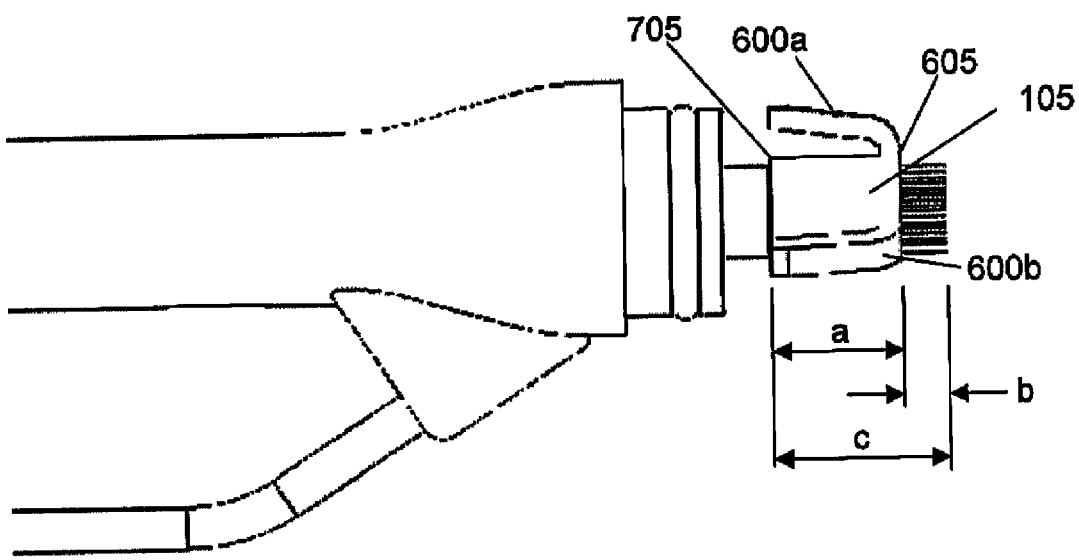
FIG. 7 shows a side view of the first implementation of the bristled tip placed on the handle and illustrates several dimensions.

FIG. 7 is a side view of bristled tip 105. Table A below shows several implementations for the various dimensions of bristled tip 105. It should be appreciated, however, that many other dimensions are possible.

TABLE A

| Dimension | First Implementation (values in mm) | Second Implementation (values in mm) |
|---|---|---|
| A | 7-13 | 10 |
| B | 2-4 | 3 |
| C | 9-17 | 13 |

According to one aspect of the invention, the length of the bristle strands from the core to their free ends may, for example, range from about 1 millimeter to about 4 millimeters. This includes, for example, less than 1 millimeter, 2, 3, and more than 4 millimeters.

In a specific implementation, support ribs 600*a*, 600*b*, and 600*c* (shown in FIG. 6) extend from the front face 605 of the bristled tip 105 to a back face 705 of the bristled tip 105 as shown in FIG. 7. However, this is not always the case. In other implementations, the support ribs may terminate before reaching the back face 705. For example, the support ribs may only extend 30 percent, 50 percent, or 75 percent of the dimension "a" of the bristled tip 105. In yet another implementation, the support ribs may extend past back face 705. Moreover, the distance that each support rib extends down the bristled tip 105 may not be the same. For example, support rib 600*a* may extend for a distance that is 50 percent the length of dimension a, while support rib 600*b* may extend for a distance that is 75 percent the length of dimension a.

Figure 8:
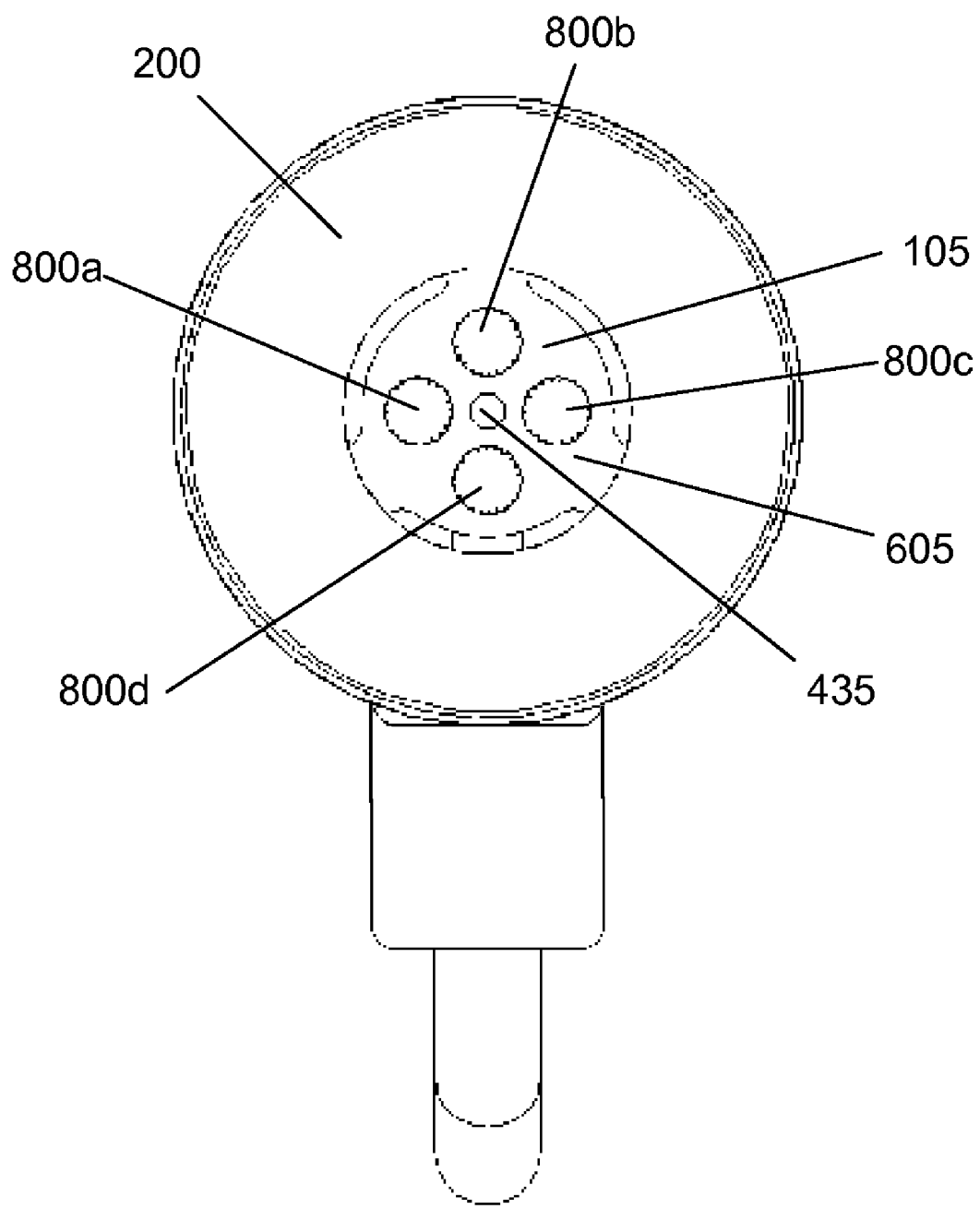
FIG. 8 shows a front view of the first implementation of the bristled tip with three groups of bristles.

FIG. 8 is a front view of the bristled tip 105 and tip holder 200. In a specific implementation, the bristled tip 105 includes four groups of bristles 800*a*, 800*b*, 800*c*, and 800*d*. In another specific implementation there may be six groups of bristles. In other implementations, there may be just one group of bristles, two, three, five, seven, eight, nine, ten, eleven, twelve, or more than twelve groups of bristles.

The groups of bristles 800*a*, 800*b*, 800*c*, and 800*d* form a ring around an opening 435 through which fluid flows out. Bristles 800*a*, 800*b*, 800*c*, and 800*d* separate the opening 435 from the skin so that fluid can flow out of the opening. In a specific implementation, opening 435 is on the same plane as face 605 of the bristled tip 105. In other implementations, opening 435 may be on a different plane. For example, opening 435 may be recessed into face 605 or opening 435 may protrude out from face 605. In an implementation where opening 435 protrudes out, the fluids exit opening 435 closer to the skin. This helps to ensure that the skin is treated with fluids before the fluids are pulled back (or suctioned) into the tip holder 200.

In a specific implementation, the surface area of opening 435 through which fluid flows out of may be about 0.5 square millimeters to about 4 square millimeters. This includes, for example, 0.6, 0.7, 0.8, 0.9, 1, 2, 3, or more than 4 square millimeters. In an implementation, the surface area of opening 453 may be less than 0.5 square millimeters.

In an implementation, the total surface area for the openings for fluid may occupy a range from about 1 percent to about 10 percent of the total surface area of the treatment head. This includes, for example, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5 percent, or more than 10 percent of the total surface area of the treatment head. In other implementations, the percentage may be less than 1 percent.

In the implementation shown in FIG. 8, the groups of bristles 800*a*, 800*b*, 800*c*, and 800*d* are equally spaced from each other, and surround opening 435. However, in other implementations, the groups of bristles may not be equally spaced from each other, may only occupy a certain region of the treatment head, or both. For example, in a specific implementation, bristles may only occupy the top half of the bristled tip 105. In this specific implementation, the bristled tip 105 may be intended to travel in a specific direction over the skin. For example, if the skin is particularly sensitive then the direction of travel may be such that the leading edge, i.e., the edge that first contacts the skin, is the edge that does not include the bristles. This allows the fluids to contact the skin before the bristles to provide, for example, lubrication or numbing agents. The trailing edge, i.e., that edge that does include the bristles can then contact the patient's skin to provide the microdermabrasion.

In yet another implementation, opening 435 may be located at a different region of the bristled tip 105, such as near an edge of the bristled tip. Furthermore, there may be more than one opening through which fluid flows out of. For example, there may be two, three, four, five, six, seven, or more than eight openings for fluid to flow out of. In a specific implementation, these openings may then surround the group or groups of bristles.

The bristles may be made from a synthetic material, natural material, or a combination of synthetic and natural materials. Synthetic materials include, for example, polyethylenes, polyamides, polymers, nylon, polybutylene terephthalate (PBT), polyvinylidene fluoride (PVDF), acetyl resins, polyesters, fluoropolymers, polyacrylates, polysulfones, thermoplastics, or combinations of these. Metal strands may also be used. Natural bristles may be made, for example, from the hair of a boar, cow, horse, mink, cashmere, buffalo, pony, goat, mongoose, oxen, squirrel, badger, weasel, or kolinsky weasel.

The bristles may contain polytetrafluoroethylene (PTFE), be treated with wax, or include other hydrophobic ingredients to ensure that fluids do not adhere to the bristles. The bristles may also contain kaolin, or other fillers or additives.

In a specific implementation, the individual strands making up the bristles may be crimped. Crimped strands may provide a softer brushing action and reduce breakage. In another implementation, the bristles may be straight. Straight bristles may provide a stiffer brushing action.

The bristles may have a stiffness grade of about 0.5 centinewtons per square millimeter to about 30 centinewtowns per square millimeter. For example, the stiffness grade may be 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 12, 14, 16, 18, 20, 22, 24, 26, 28, or 29 centinewtons. Depending on the application, the stiffness grade may be more than 30 centinewtons or less than 0.5 centinewtons.

In still another aspect, a bristled tip 105 may include a mixture of bristle groups and strands having differing lengths, materials, cross-sectional areas, characteristics, or combinations of these. For example, a specific implementation may include a directional bristled tip. The leading edge of bristles may have a higher stiffness grade, or be more abrasive, than the trailing edge of bristles. This allows, for example, the more abrasive bristles to contact the skin first and remove a first layer of skin cells. Since the second layer of skin cells may be more sensitive, the trailing edge of bristles may have a lower stiffness grade, or be less abrasive so as to not irritate the skin.

In a specific implementation, the bristle strands may have uniform cross-sectional areas. In other implementations, the cross-sectional areas may vary across bristle strands.

A group of bristles may form a diameter that ranges from about 0.5 millimeters to about 20 millimeters where a larger treatment head is used. This includes 0.6, 0.7, 0.8, 0.9, 1, 2, 3, 4, 5, 10, 15, or more than 20 millimeters. The diameter may also be less than 0.6 millimeters. Where a group of bristles do not define a circular cross-section, the term "diameter" may be used to refer to the diameter of a circle that circumscribes the largest cross section of the noncircular group of bristles.

The total surface area for a group or groups of bristles at their free end may range from about 8 square millimeters to about 320 square millimeters. This includes for example, 9, 10, 11, 12, 13, 14, 15, 16, 17, 18, 19, 20, 25, 30, 40, 50, 100, 150, 200, 250, 300, or more than 320 square millimeters. The surface area may also be less than 8 square millimeters. The smaller surface areas may be more appropriate where the area for microdermabrasion is small such as a patient's face. The larger surface areas may be more appropriate where the area for microdermabrasion is large such as a patient's back, chest, arms, or legs.

In a specific implementation, a group of bristles may have a similar cross-sectional area throughout the length of the group of bristles. However, in other implementations, the cross-sectional area will vary. For example, in the case of a group of crimped bristles, the cross-sectional area at the free end of the bristles may be larger than the cross-sectional area of the bristles at their crimped end. This is because crimped bristles have a tendency to splay out at their free ends.

In an implementation, the total surface area for all the groups of bristles may occupy a range from about 17 percent to about 60 percent of the total surface area of the bristled tip. This includes, for example, 18, 19, 20, 21, 22, 23, 24, 25, 30, 35, 40, 45, 50, 55, or more than 60 percent. In other implementations, the percentage may be less than 17 percent.

In a specific implementation, each group of bristles has a reference point. The reference point may be the center of the group of bristles if, for example, the bristle strands are arranged to form circular shapes. Alternatively, the reference point may be defined as some other point, so long as the definition is consistent among the groups of bristles.

A group of bristles may be separated by a distance of about 0.5 millimeters to about 5 millimeters from their respective reference points. This includes, for example, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4, 4.5 or more than 5 millimeters. In other implementations, the distance will be less than 0.5 millimeters.

The bristles may be attached to the bristled tip 105 using, for example, stapling, fusion, gluing, or other attachment method, or combinations of these. In stapling, a group of bristles is folded over a staple and forced into a cavity in the tip. In fusion, the bristles are fused with heat and the resulting tuft is molded with the tip.

In a specific implementation, the bristles are distributed along a planar surface 605 of bristled tip 105. However, in other implementations, the surface may not be planar. For example, the surface may be convex or concave. The bristles may also be distributed over a helical surface. These nonplanar surfaces may be used, for example, on skin surfaces that are not planar such as the edge of patient's jawline or the curved surface of a patient's forehead. Bristles distributed on a nonplanar surface may be better able to fully contact the patient's skin while maintaining the same level of pressure across all the bristles.

In another implementation, one or more groups of bristles may be attached to springs within the bristled tip 105. These springs may then compress as the bristled tip 105 is moved over the nonplaner surfaces of a patient's skin. These springs allow the bristles to conform to nonplaner skin surfaces.

Figure 9:
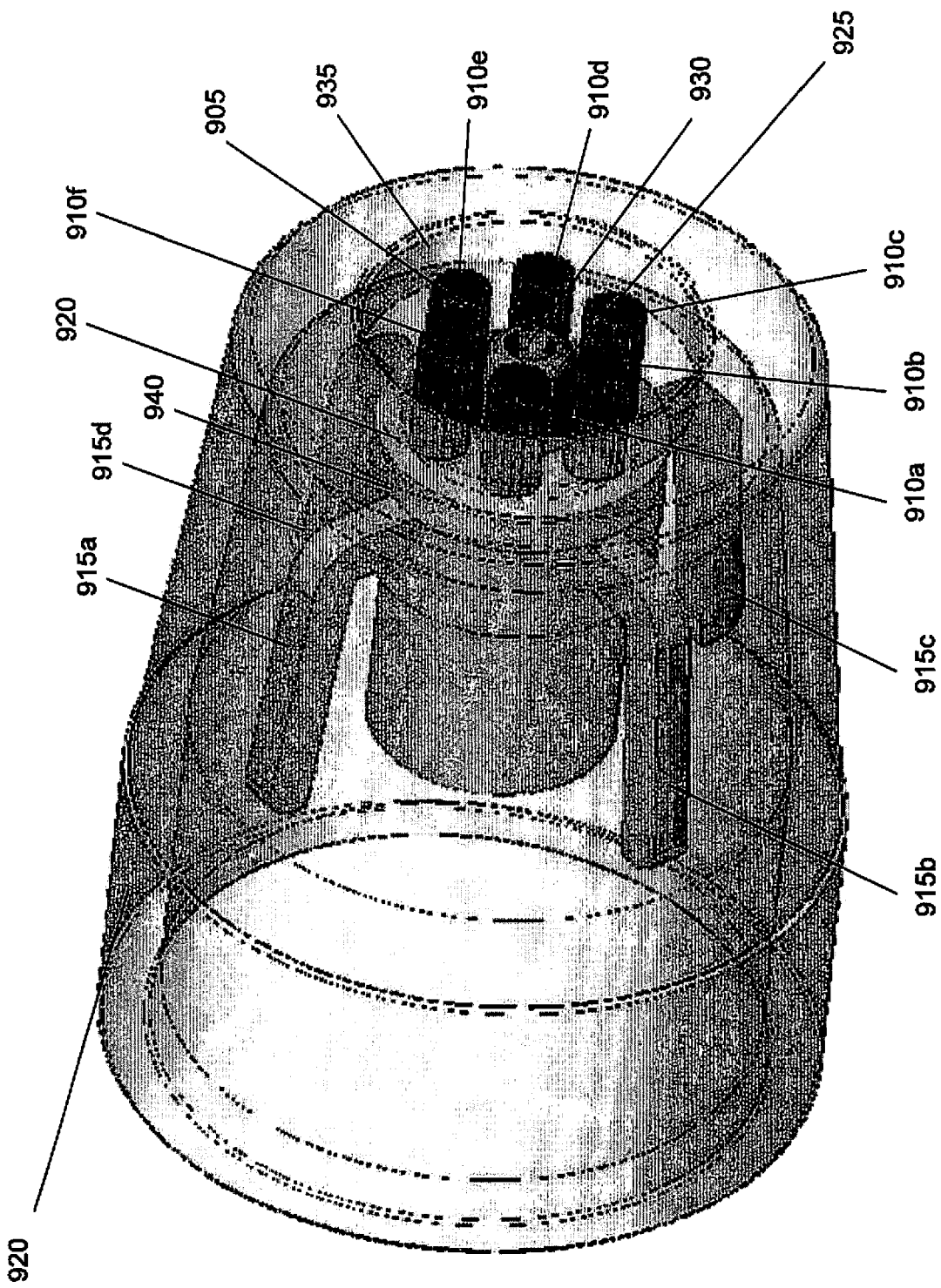
FIG. 9 shows a perspective view of a second implementation of the bristled tip with six groups of bristles in the tip holder.

FIG. 9 shows an example of a specific implementation of a bristled tip 905. In a specific implementation, bristled tip 905 may have six groups of bristles (910*a*, 910*b*, 910*c*, 910*d*, 910*e*, 910*f*), four support ribs (915*a*, 915*b*, 915*c*, 915*d*) which are offset from a face 920 the bristled tip 905, and an opening 930 which is at the end of a nipple 925.

Nipple 925 extends some distance away from the face 920 of the bristled tip. The opening may extend from about 30 percent to about 75 percent the length of the bristles, including, for example, less than 30 percent, 50 percent, or more than 75 percent the length of the bristles. This nipple places opening 930 closer to the skin and helps to ensure that the fluid contacts the skin before being vacuumed, suctioned, or sucked back into tip holder 920.

Support ribs 915*a*, 915*b*, 915*c*, and 915*d* may be offset from face 920 of the bristled tip and attached at any point along the length of the bristled tip 905. The ribs or prongs of the tip generally conform to an inside surface of a tip holder into which this tip fits. In a specific implementation, the distance for the offset is the same for all support ribs 915*a*, 915*b*, 915*c*, and 915*d*. In other implementations, the support ribs may be offset at different distances. For example, support rib 915*a* may be offset from face 920 by 0.5 millimeters, while support ribs 915*a*, 915*b*, and 915*c* may be offset from face 920 by 1 millimeter.

Offsetting the support ribs allows, for example, an uninterrupted annular space 940 to be created near the front of the tip holder 920. This allows fluids to more easily pass back into tip holder 920 without being blocked by any structures.

In a specific implementation, a tip holder 920 used to hold bristled tip 905 may be the same as tip holder 200 (see, e.g., FIG. 5) that is used to hold bristled tip 105 (see e.g., FIG. 5) which in a specific implementation has four groups of bristles. However, in other implementations, tip holder 920 may be different from tip holder 200. For example, tip holder 920 may have a larger opening 935 to accommodate the additional bristle groups.

Figure 10:
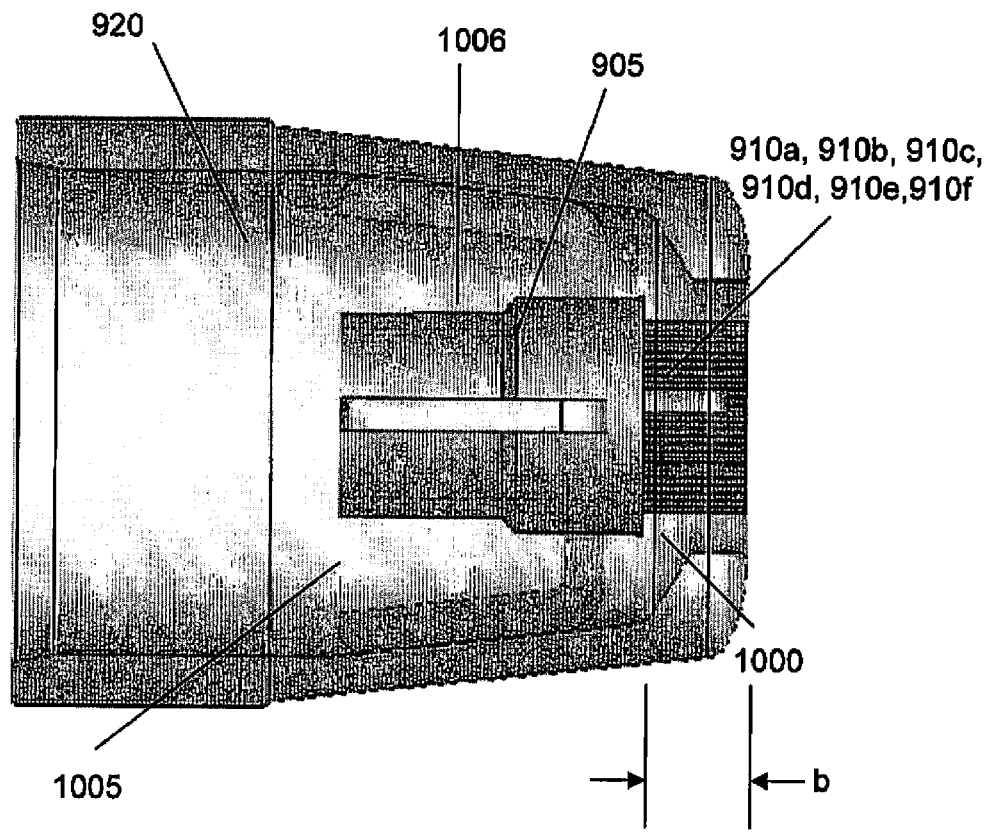
FIG. 10 shows a side view of a second implementation of the bristled tip in the tip holder.

FIG. 10 shows a side view of tip holder 920 placed over bristled tip 905 and the resulting annular space 1005. In a specific implementation, each length "b" of a bristle strand is the same and extends to an opening 1000 of the tip holder 920 as shown in FIG. 10.

In other implementations, bristles 910*a*, 910*b*, 910*c*, 910*d*, 910*e*, 910*f* may extend past opening 1000. The bristles may extend past opening 1000 by about 0.5, 1, 2, 3, 3.1, 3.2, 3.3, 3.4, 3.5, 4, 5, or more than millimeters. The bristles may also extend past the opening 1000 by a distance that is less than 0.5 millimeters.

In yet another implementation, the free ends of bristles 910*a*, 910*b*, 910*c*, 910*d*, 910*e*, 910*f* may terminate before reaching opening 1000. The bristles may terminate from about 0.5, 1, 2, 3, 3.1, 3.2, 3.3, 3.4, 3.5, 4, 5, or more than 5 millimeters from opening 20*a*. The bristles may also terminate at a distance less than 0.5 millimeters from opening 1000.

Figure 11:
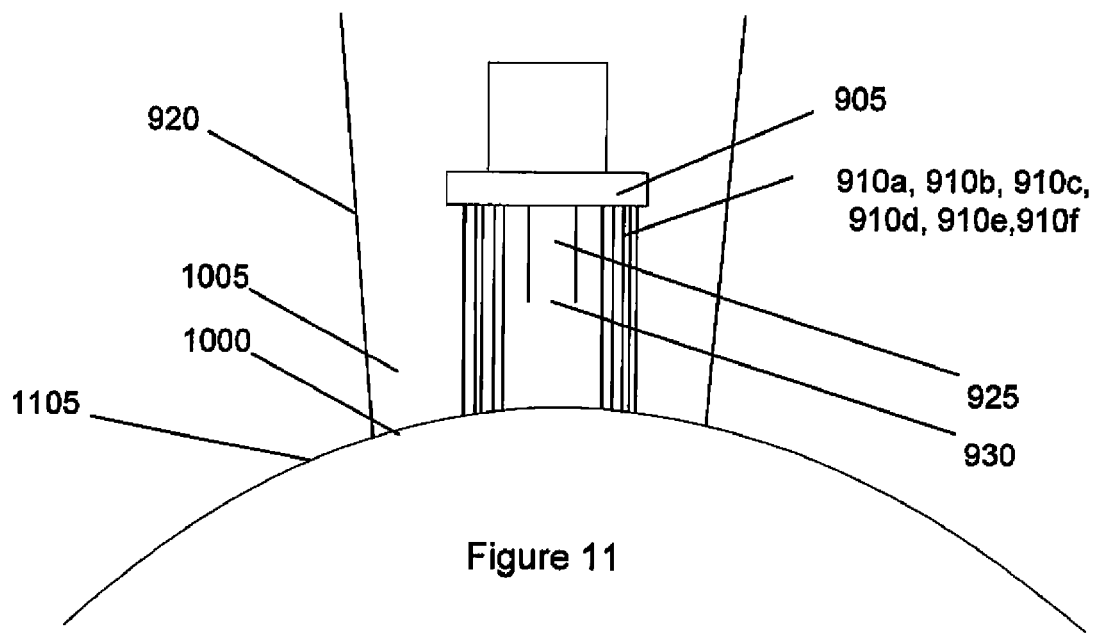
FIG. 11 shows a line diagram representation of the invention in use with the bristled tip.

For example, in FIG. 11, the bristles 910*a*, 910*b*, 910*c*, 910*d*, 910*e* terminate before reaching opening 1000. This allows a skin 1105 to be pulled into opening 1000 to seal opening 1000, which causes a closed loop to be formed. The skin then contacts the bristles. Simultaneously, fluid flows out of opening 930, treats the patient's skin and is then removed through the vacuum in annular space 1005. Since the vacuum in the annular space surrounds both the bristles 910*a*, 910*b*, 910*c*, 910*d*, 910*e* and the opening 930 that the fluid exits from, there is very spent fluid or debris that needs to be later removed from the patient's skin.

In a specific implementation, the lengths of the bristles may vary. For example, the lengths of the bristles may vary such that the free ends of the bristles form a diagonal plane. This particular implementation allows wand 10 (see FIG. 1) to be held at the angle of the diagonal plane, which some users may find more comfortable, while still having all the bristles contact the skin.

As another example, the lengths of the bristles may also vary to form a concave or convex plane, or an angular or serrated profile, or another nonplanar surface, profile, or topography. These nonplanar implementations allow, for example, the bristled tip to follow the concave and convex contours of a patient's skin.

In a specific implementation, bristled tip 905 also includes a body 1006 with cross-sectional area of varying values. The front third section of bristled tip 905 tapers into a smaller cross-sectional area for the back two-thirds section.

Figure 12:
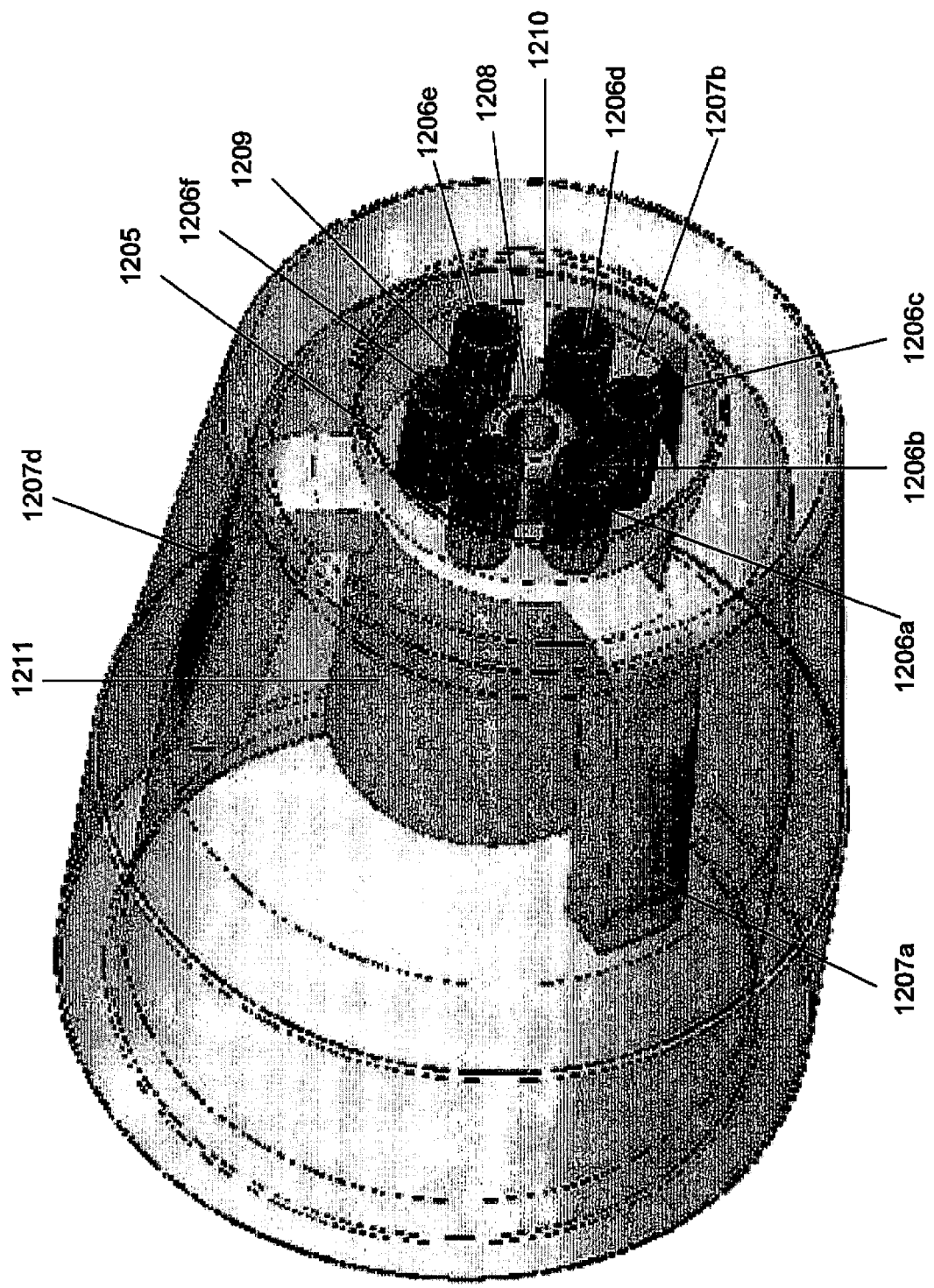
FIG. 12 shows a perspective view of a third implementation of the bristled tip with six groups of bristles in the tip holder.

FIG. 12 shows a specific implementation of a bristled tip 1205. In a specific implementation, bristled tip 1205 may have six groups of bristles (1206*a*, 1206*b*, 1206*c*, 1206*d*, 1206*e*, 1206*f*), three support ribs or prongs (1207*a*, 1207*b*, 1207*c*) which are attached flush with a face 1208 on the bristled tip 1205, and an opening 1209 at the end of a nipple 1210.

It should be appreciated that there may be many different combinations of bristled tips that include, for example, different numbers of bristle groups, support ribs and fluid openings, different attachment positions for support ribs, or different positions for fluid openings. For example, in a specific implementation, the bristled tip may include two support ribs and three groups of bristles. The support ribs may not be equally spaced from each other. For example, instead of being spaced at 0 degrees and 180 degrees, the support ribs may be spaced at 0 degrees and 92 degrees. Furthermore, a first support rib may be attached flush with the face of the bristled tip while a second support rib is offset 0.5 millimeters from the face of the bristled tip.

In a specific implementation, the tip may not be a bristled tip. Instead the tip may be a smoothed surface tip or a tip containing other abrasive elements.

In a specific implementation, bristled tip 1205 includes a body 1211 that has a constant cross sectional area.

Figure 13:
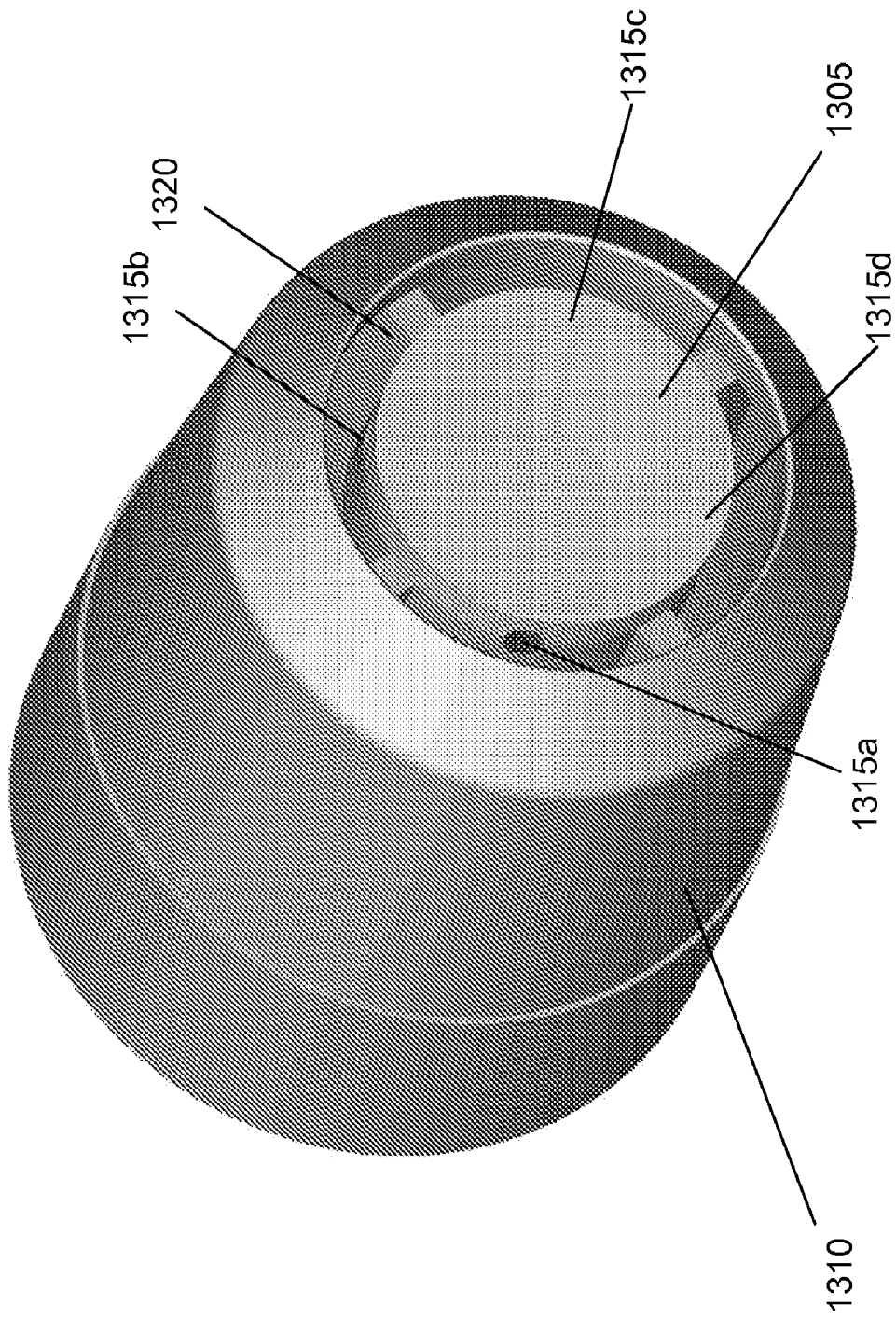
FIG. 13 shows a perspective view of a first implementation of an abrasive tip, tip holder, openings for fluid, and an annular space in which a vacuum removes fluid, skin particles, and other debris.

FIG. 13 shows an example of an abrasive tip 1305 that does not have bristles. Abrasive tip 1305 is shown placed within a tip holder 1310. Fluid flows out of openings 1315*a*, 1315*b*, 1315*c*, and 1315*d*. The fluids contact the skin and are then pulled back into a vacuum in an annular space 1320. In a specific implementation, the openings are equally spaced from each other around the abrasive tip 1305. Thus, fluids are able to completely and uniformly surround the target area of skin that is being treated. These fluids may, for example, help to dislodge debris on the skin to increase the effectiveness of the abrasive tip 1305.

Figure 14:
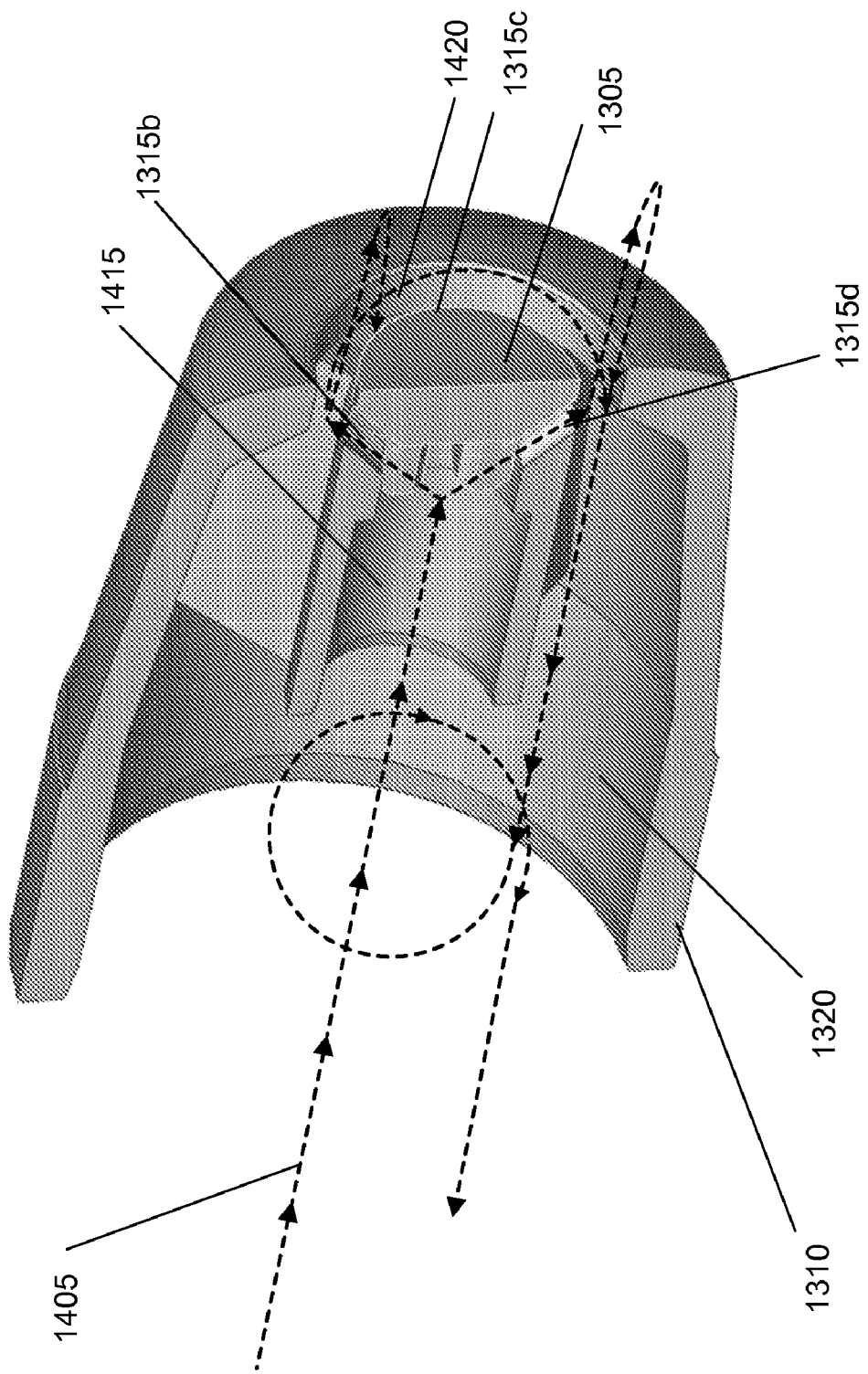
FIG. 14 shows a perspective view of a vacuum loop flow path for the abrasive tip and tip holder.

FIG. 14 shows a cross-sectional view of tip 1305 and tip holder 1310. A vacuum loop 1405 shows the flow of fluids. Arrows on the vacuum loop 1405 indicate the direction of fluid travel. As described in earlier figures and with reference to FIG. 1, vacuum source 40 pulls fluids from fluid reservoir 71, through tube 14 and into wand 10.

Tip holder 1310 as shown in FIG. 14 is connected to wand 10. Fluids flow through a tube 1415. The fluids then exit through one or more openings 1315*a* (see FIG. 13), 1315*b*, 1315*c*, and 1315*d* and then exit an opening 1420 on the tip holder 1310. The fluids contact the skin and are then pulled back into opening 1420 by the vacuum in an annular space 1320.

With reference to FIG. 1, the fluids are then pulled into vacuum line 42 where they are collected in collection reservoir 51.

Figure 15:
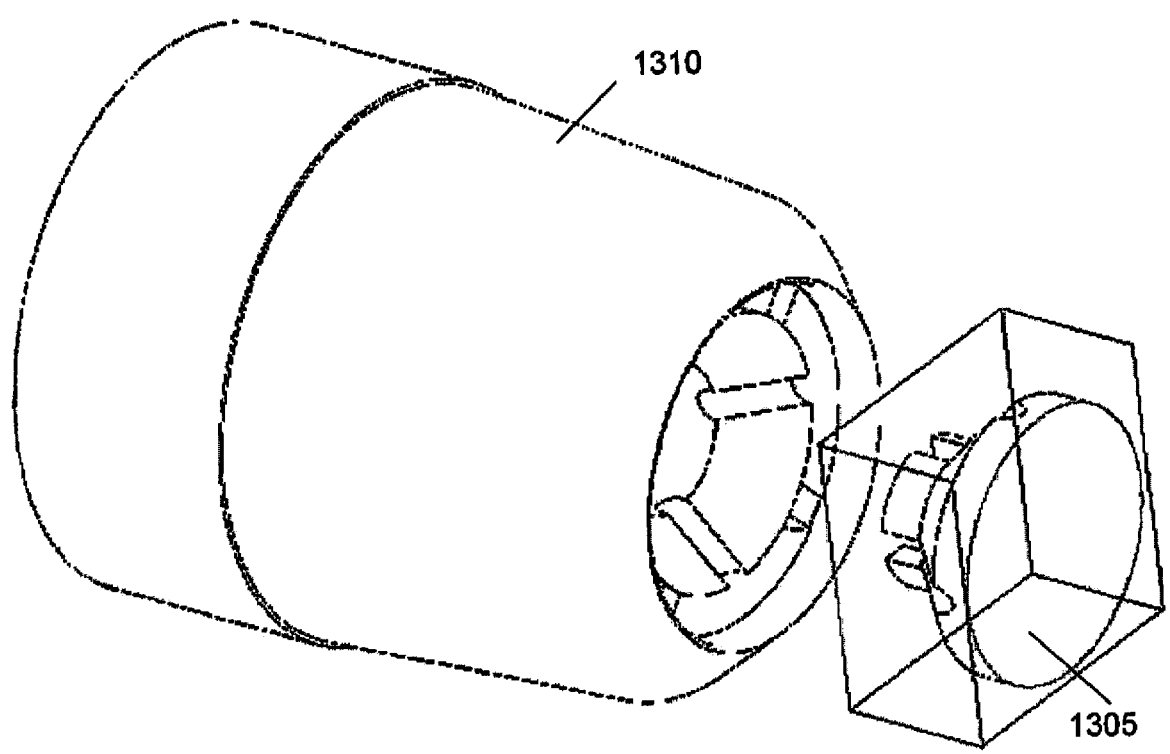
FIG. 15 shows a perspective view of the assembly of the first implementation of the abrasive tip and tip holder.

FIG. 15 shows a specific implementation where the tip holder 1310 is a separate unit from the abrasive tip 1305. In another implementation, tip holder 1310 and abrasive tip 1305 may be one unit. For example, tip holder 1310 and abrasive tip 1305 may be integrally molded or machined.

Figure 16:
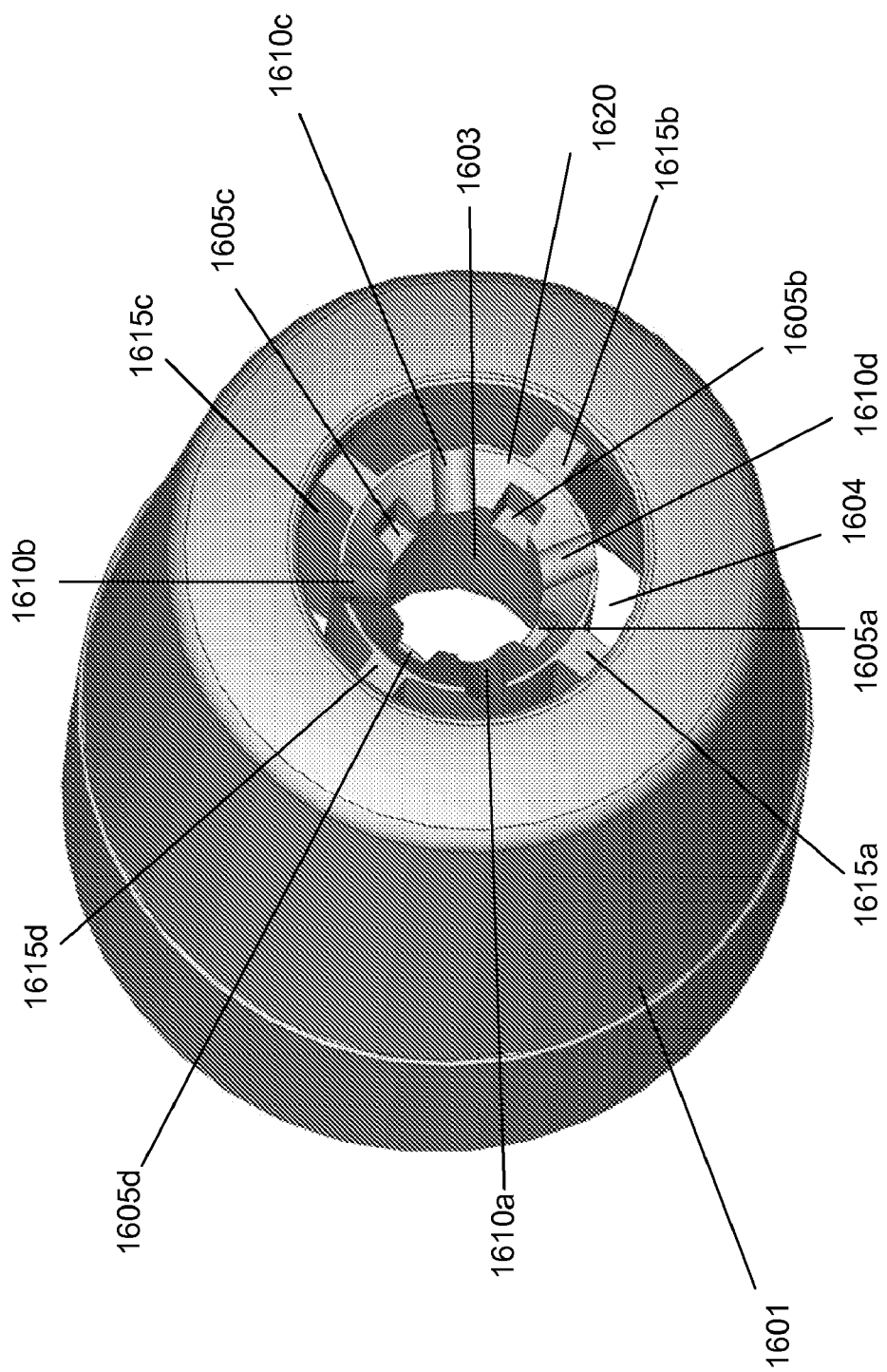
FIG. 16 shows a perspective view of a second implementation of a tip holder which includes channels to direct fluid, notches that accept keys on the abrasive tip, and the annular space.

FIG. 16 shows the front of a specific implementation of a tip holder 1601 into which an abrasive tip 1602 is placed. Tube 1603 is surrounded by annular space 1604. Support ribs 1615*a*, 1615*b*, 1615*c*, and 1615*d* support tube 1603 within tip holder 1610.

Tip holder 1610 includes channels 1610*a*, 1610*b*, 1610*c*, and 1610*d* that are on a front surface 1620 of tube 1603. The front surface 1620 is angled in towards the interior of tube 1603. This then allows fluid that flows through tube 1603 to then be redirected along the channels.

In a specific implementation, the channels are equally spaced around the perimeter of tube 1603. For example, in an implementation where tube 1603 has a circular cross section and four channels, the channels may located at 0, 90, 180, 270, and 360 degrees. In other implementations, there may be less than four channels (e.g., one, two, or three) or more than four channels (e.g, five, six, seven, or eight). Moreover, the channels may not necessarily be equally spaced from each other.

Tip holder 1610 may also include notches 1605*a*, 1605*b*, 1605*c*, and 1605*d*. There may be any number of notches. For example, there may be no notches, one, two, three, four, five, six, or more than 6 notches.

In a specific implementation, there may be a total of four support ribs (1615*a*, 1615*b*, 1615*c*, 1615*d*) which support tube 1603 in annular space 1604. Specifically, the annular space is formed between the inner surface of the tip holder and the exterior surface of tube 1603. Generally, the less volume or space taken up by the ribs enlarges the volume of the annular space.

In a specific implementation, fluids and abraded tissues are vacuumed back into the wand through the annular space. This annular space creates an annular vacuum region that surrounds the passageway of the wand where fluids flow to the tip. The volume of the annular space may vary depending on the specific design, but generally, larger volume annular spaces will help prevent potential blockage or other similar problems, especially when compared to pores or other structures that will restrict flow more.

The four support ribs are equally spaced around the perimeter of tube 1603. For example, the an angle between the support ribs is given by 360 degrees divided a total number of support ribs (e.g., for four support ribs, the angle is 90 degrees; for three support ribs, the angle is 60 degrees; and for five support ribs, the angle is 72 degrees). In other implementations, the support ribs may not be equally dispersed around the perimeter of tube 1603.

While tube 1603 is shown with a circular cross-sectional area, this not always the case. For example tube 1603 may be a square tube, rectangular tube, triangular tube, elliptical tube, or any other hollow shape.

In the implementation shown in FIG. 16, the ends of the support ribs are planar. However, in other implementations, the end of the support ribs may have an outwardly (e.g., convex) angular or beveled surface or edges. This allows fluid to more easily flow past.

In other implementations, there may be less than four support ribs. For example, there may be no support ribs, one, two, or three support ribs. In another implementation, there may be more than four support ribs, including for example, five, six, or more than seven support ribs.

It should be appreciated that any arrangement or number of support ribs (including no support ribs) is possible so long as fluids are able to pass through the vacuum created in annular space 1320.

Consequently, a flange, or a portion of a flange may be used between the tube 1603 and the tip holder 1601 either with or without one or more support ribs. For example, where a flange completely encircles tube 1603, the flange may contain one or more openings which allow fluids to pass from the front of tip holder 1601 to the back of tip holder 1601.

In a specific implementation, the support ribs are molded or machined as an integral part of the tip holder 1601.

In a specific implementation, tip holder 1601 is formed as a result of machining. However, in other implementations, tip holder 1601 may be formed using other manufacturing techniques such as casting, molding, injection molding, etching, or a combination of these including machining.

Figure 17:
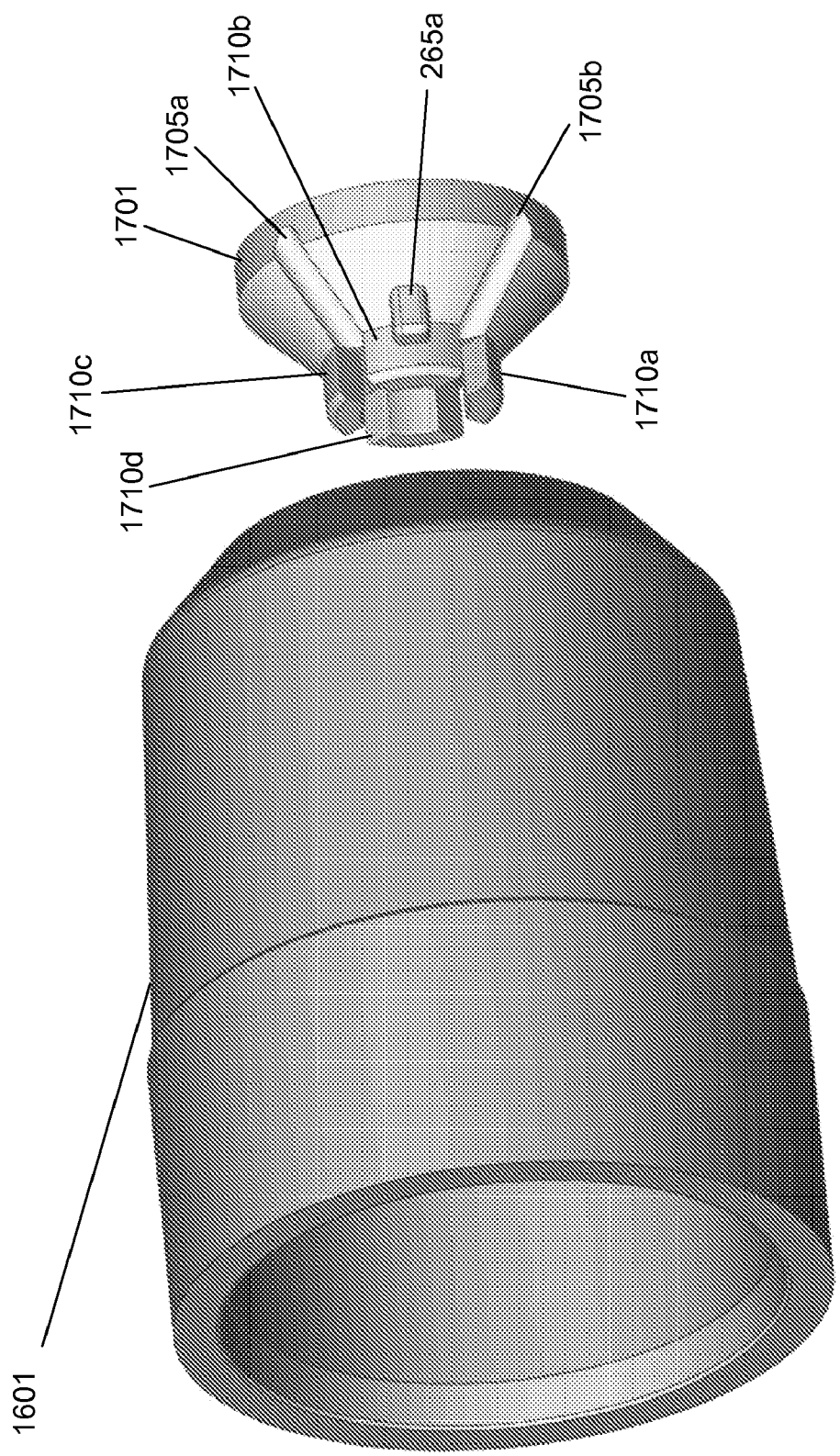
FIG. 17 shows a perspective view of the back side of an abrasive tip which includes channels to direct fluid, a key that fits into notches in the tip holder, and collars which support the abrasive tip.

FIG. 17 shows the back of a specific implementation of an abrasive tip 1701. In a specific implementation, the abrasive tip 1701 includes channels 1705*a*, 1705*b*, 1705*c*, and 1705*d*. Channels 1705*c* and 1705*d* are not shown due to the perspective view of the drawing. Abrasive tip 1701 also includes collars 1710*a*, 1710*b*, 1710*c*, and 1710*d* and a key 265*a*.

In a specific implementation, the channels 1705*a*, 1705*b*, 1705*c*, and 1705*d* are equally spaced around the perimeter of the abrasive tip 1701. For example, in an implementation where the abrasive tip 1701 has a circular cross-section and four channels, the channels may be located at 0, 90, 180, 270, and 360 degrees. In other implementations, the abrasive tip 1701 may include less than four channels, such as no channels, one channel, two channels, or three channels. In another implementation, there may be more than four channels, including, for example, five, six, seven, or more than eight channels.

Channels 1705*a*, 1705*b*, 1705*c*, and 1705*d* in the abrasive tip 1701 align with the channels 1610*a*, 1610*b*, 1610*c*, and 1610*d* in the tip holder 1601 as shown in FIG. 16. When these channels are aligned they form the openings 1315*a*, 1315*b*, 1315*c*, and 1315*d* as shown in FIG. 13 that fluid flows out of. For example, with reference to FIGS. 13, 16, and 17, channel 1705*a* in the abrasive tip 1701 may align with channel 1610*a* in the tip holder 1601 to form opening 1315*a*. Channel 1705*b* in the abrasive tip 1701 may align with channel 1610*b* in the tip holder 1601 to form opening 1315*b*. Channel 1705*c* in the abrasive tip 1701 may align with channel 1610*c* in the tip holder 1601 to form opening 1315c. Channel 1705d in the abrasive tip 1701 may align with channel 1610d in the tip holder 1601 to form opening 1315d.

The FIGS. 16 and 17 show U-shaped or semicircular shaped channels or grooves which, when aligned, form circular shaped openings. However, this is not always the case. In other implementations, the openings formed may have the shape of a polygon such as a rectangle or square, or the shape may be elliptical or oval. Furthermore, there may be a combination of differently shaped openings which are formed using differently shaped channels.

The U-shaped or other shaped grooves in the tip combine (or mate) with similar grooves in the tip holder to form a complete channel, through which the fluid will flow. Because of the design of the invention, when the tip and tip holder are separated, the grooves are exposed so that they can more easily be examined and cleaned. This will allow a user to more easily clean or clear the fluid channels in the tip, thus helping prevent clogging of the fluid channels (e.g., after use, the fluid has residue that after the fluid evaporates can clog a tip).

In a specific implementation, the openings allow fluid to flow out around the perimeter of the abrasive tip 1701 as opposed to the front surface of the abrasive tip 1701. This prevents the tissue that is being treated from occluding the openings.

However, in other implementations, there may be openings on the surface of the abrasive tip 1701 itself. For example, there may be an opening for fluid located in the center of the abrasive tip 1701. Additionally, there may also be a combination of openings at different locations. For example, there may be openings located at or near the perimeter of the abrasive tip 1701 and an opening or openings on the surface of the abrasive tip 1701.

In a specific implementation, the openings all have the same cross-sectional areas. The cross-sectional areas may range, for example, from about 0.05 square millimeters to about 20 square millimeters. For example, the cross-sectional areas may be 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.5, 4, 4.5, 5, 10, 15, or 19.9 square millimeters. Depending on the application, the cross-sectional area may be less than 0.5 square millimeters, or greater than 20 square millimeters. In other implementations, the cross-sectional areas of the openings will be different. For example, one opening may have a cross-sectional area of 0.3 square millimeters, while another opening may have a cross-sectional area of 0.5 square millimeters.

In yet another implementation, the cross-sectional area of a particular opening may vary from one end of the opening to the opposite end. This allows, for example, varying the flow rate and velocity of fluid exiting from the openings.

In a specific implementation key 265a in the abrasive tip 1701 fits into any of notches 1605a, 1605b, 1605c, and 1605d in tip holder 1310 as shown in FIG. 16. Thus, this specific implementation provides for four different positions for abrasive tip 1701 to be positioned in tip holder 1310.

There may be any number of keys. For example, there may be no keys, one, two, three, four, five, or more than five keys. In a specific implementation, the number of keys on the abrasive tip 1701 will be the same as the number of notches on the tip holder 1601. In another implementation, the number will be different. For example, there may be fewer keys on the abrasive tip 1701 than notches on the tip holder 1601.

In a specific implementation, the sizes of the keys and notches are the same. In another implementation, the sizes may be different. In yet another implementation, the notches may be on the abrasive tip 1701 while the keys are on the tip holder 1601, or there may be a combination arrangement. That is, an implementation may have a combination of keys and notches on both the abrasive tip 1601 and tip holder 1701.

The key or keys ensure that the channels 1610a, 1610b, 1610c, and 1610d in the tip holder 1601 and channels 1705a, 1705b, 1705c, and 1705d in the abrasive tip 1701 are properly aligned to form the openings 1315a, 1315b, 1315c, and 1315d in FIG. 13 through which fluid flows out. The key or keys also ensure that tip 1701 does not rotate during the microdermabrasion session and move the channels out of alignment. In other implementations, however, it may be desirable to have a rotating tip in order to provide additional microdermabrasion action (i.e., tip rotates or spins during use).

In a specific implementation, the keys may also be used to specifically misalign certain channels in the tip holder 1601 and abrasive tip 1701 in order to not form an opening for fluid to exit. Thus, the amount of fluid exiting may be adjusted by misaligning the channels in the abrasive tip 1701 with the channels in the tip holder 1601.

In a specific implementation where there is a particular direction of travel for the abrasive tip 1701, the keys may also be used to ensure that the abrasive tip 1701 is properly positioned along the particular direction of travel.

Collars 1710a, 1710b, 1710c, and 1710d slide into the tip holder 1601. The collars 1710a 1710b, 1710c, and 1710d are positioned between the channels 1705a, 1705b, 1705c, and 1705d in the abrasive tip 1701. This allows fluid to flow out of the openings formed by aligning the channels in the abrasive tip 1701 with the channels in the tip holder 1601.

The number of collars may vary. Typically, the number of collars will be dependent on the number of channels. For example, if there are four channels, then there will be four collars. However, this is not always the case. In other implementations, the number of collars will be different from the number of channels. There may be more channels than collars, or there may be fewer channels than collars.

Figure 18:
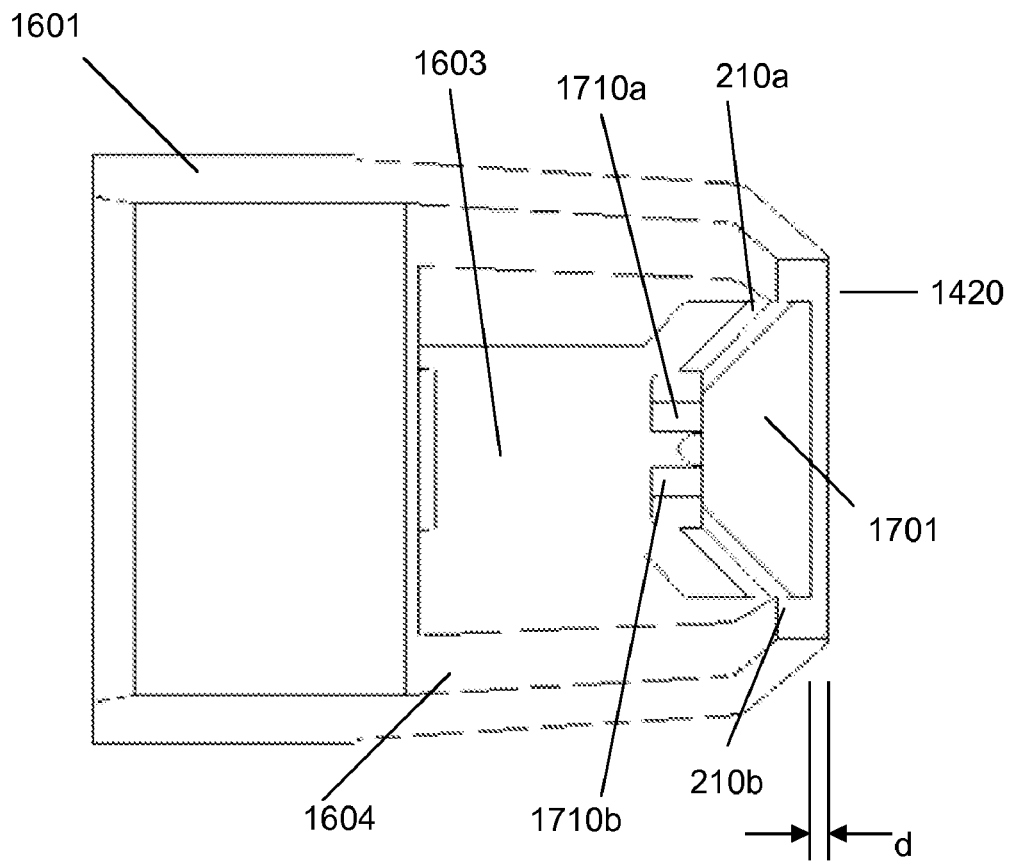
FIG. 18 shows a cross-sectional view of the abrasive tip and tip holder.

As shown in the cross-sectional view in FIG. 18, the collars 1710a, 1710b, 1710c (not shown) and 1710d (not shown) help to support the abrasive tip 1701 in the tip holder 1601. In a specific implementation, the abrasive tip 1701 is held in tip holder 1601 using a friction fit between the collars and the tip holder 1601. The pressure of the abrasive tip 1701 against the skin and the vacuum in annular space 1604 also helps to hold the abrasive tip 1701 in the tip holder 1601.

However, in other implementations, other types of fastening interfaces may be used. For example, the abrasive tip 1701 may be held in the tip holder 1601 using magnets, a snap fit (e.g., cantilever snap fit), threads, a screw or screws, or combinations of these. When using a snap fit interface, for example, a ridge may be located on one or more of the collars. This ridge may then snap into a recess in tip holder 1601.

When using a screw, for example, the screw may be inserted through the abrasive tip 1701 and threaded into a plate in located in tube 1603. In this particular implementation, the screw is typically recessed into the abrasive tip 1701. This ensures that the head of the screw does not scrape the patient's skin.

The type of drive design on the screw may vary. For example, the drive may be slotted, a Phillips, a Pozidriv, a torx, a hex, a Robertson, a tri-wing, a Torq-set, a spanner head, or a triple square.

In a specific implementation, a plate in tube 1603 that the screw threads into will still allow fluid to pass though. This may be accomplished where, for example, the plate is a cross bar that spans the inner walls of tube 1603. In this case, fluid would pass around the cross bar. In another implementation, the plate may contain perforations that allow fluid to pass through. In yet another implementation, the plate may be smaller than the cross-sectional area of the tube 1603 and be held in place with one or more supporting spokes attached to the inner walls of the tube 1603.

The screw may come into contact with fluids. Thus, in a typical implementation, the screw will be made of a material that will not react with the fluids. For example, the screw may be stainless steel, zinc coated steel, galvanized steel, aluminum, or plastic. The screw may be metric or English threaded.

FIG. 18 also shows that abrasive tip 1701 is recessed into tip holder 1601 by a distance d. This allows, for example, the skin to be pulled into opening 1420 in order to seal opening 1420 and have the skin contact abrasive tip 1701. Distance d may range from about 0.01 millimeters to about 2 millimeters. This includes, for example, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or more than 2 millimeters. In other implementations, d may be less than 0.01 millimeter.

Figure 19:
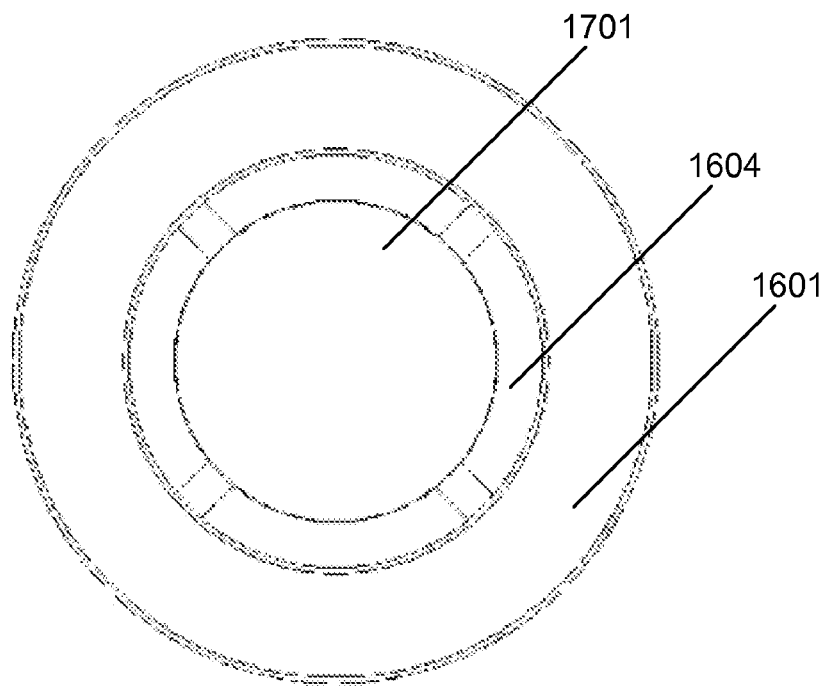
FIG. 19 shows a front view of the abrasive tip, tip holder, and the annular space around the abrasive tip.

FIG. 19 shows the front of abrasive tip 1701 and tip holder 1601. Annular space 1604 surrounds abrasive tip 1701. In a specific implementation, the surface of abrasive tip 1701 may be formed by fusing (e.g., gluing, imbedding) abrasive particles to the surface. Examples of abrasive coatings could include diamond, silicone carbide, magnesium oxide, aluminum oxide, and the like, or combinations of these. The abrasive surface may also be formed by applying an adhesive-backed paper substrate to the surface, knurling, machining, laser treatment or otherwise mechanically or chemically treating the surface. The abrasive surface may also include an abrasive open screen with bonded abrasive particles.

The abrasive particles are generally of a size ranging from about 50 grit to about 300 grit, including for example, 100 grit and 120 grit. The abrasive particles may be carborundum (aluminum oxide) or sodium bicarbonate, or other, or combinations of these. The coarser particles (at the lower ends of the grit ranges) may be provided for use in initial treatments, while finer particles (at the higher ends of the grit ranges) may be employed for later treatments.

In a specific implementation, the abrasive tip 1701 is intended for single-use only. This is because debris, such as skin particles, may become lodged within the abrasive tip 1701. The debris may reduce the abrasive properties of the abrasive tip 1701. Additionally, abrasive particles may become detached from the abrasive tip 1701. It may also be difficult to properly sanitize the abrasive tip 1701 to remove the lodged debris. In a specific implementation, abrasive tip 1701 may include structures that break-away when abrasive tip 1701 is removed from the tip holder 1601. This safeguard ensures that the abrasive tip 1701 is not erroneously reused. This also protects patients from coming into contact with abrasive tips that have been contaminated with debris from other patients.

In another implementation, abrasive tip 1701, the spent fluids, or both may be intended for sterilization and repeated use.

Annular space 1604 surrounds the abrasive tip 1701 This allows spent fluids and removed skin particles to be pulled back into the vacuum in annular space 1604. Thus, little or no spent fluids or skin particles remain on the patient's skin that will later require additional cleaning.

In a specific implementation, the surface area of the annular space may range from about 15 square millimeters to about 30 square millimeters. This includes, for example, less than 15, 16, 17, 18, 19, 20, 21, 22, 23, 24, 25, 26, 27, 28, 29, or more than 30 square millimeters. The surface area of the annular space depends, in part, on the size of the abrasive tip 1701. A ratio of the surface area of an annular space to the surface area of the abrasive tip 1701 may range from about 1:0.5 to about 1:5. This includes, for example, ratios of 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, or more than 1:5. However, in other implementations, the ratio may be less than 1:0.5.

FIG. 20A and FIG. 20B show a front view of a specific implementation of two differently sized abrasive tips 2001, 2005 and the corresponding tip holders 2002, 2010. In a specific implementation where circular shaped abrasive tips and tip holders are used, abrasive tips 2001 and 2005 may have diameters of 6 millimeters (d1) and 9 millimeters (d3), respectively.

An opening 2011 on tip holder 2010 may likewise be larger than an opening 2003 on tip holder 2002 in order to accommodate the larger abrasive tip 2005.

However, the outside diameters (d2 and d4) of tip holders 2002 and 2010 may be the same. This allows, the same wand 10 (see FIG. 1) to be used with varying abrasive tip sizes.

It should be appreciated that there may be many more sizes of abrasive tips besides the 6 millimeter and 9 millimeter diameters shown in FIG. 20A and FIG. 20B. The size or surface area of the abrasive tips may vary greatly. This depends, in part, on the skin surface to be treated.

For example, the surface area of the abrasive tips may range from about 25 square millimeters to about 350 square millimeters. Abrasive tips having smaller surface areas such as 28.3 square millimeters or 63.6 square millimeters may be used where the area to be treated is small such as a patient's cheek. The smaller abrasive tips may also offer more control when the area to be treated is adjacent sensitive areas such as around eyes or lips. Abrasive tips having larger surface areas such as 314 square millimeters may be used to treat larger areas such as arms, legs, torsos, or backs. Where, for example, circular shaped abrasive tips are used, the diameter may range from 4 millimeters to 20 millimeters. This includes, for example, less than 4 millimeters, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or more than 20 millimeters in diameter.

The abrasive tips may also be formed in different shapes other than circles, such as, ellipses, ovals, rectangles, or squares, or any other shape that substantially maintains an annulus or other flow paths that would substantially surround the abrasive tips. The shapes may include edges that are concave, convex, curved, straight, or combinations of these.

Although this specific implementation shows two different tip holders (2002, 2010) being used with two different sized abrasive tips (2001, 2005), this is not always the case. For example, the tip holder 2010 for the larger abrasive tip 2005 may also be used to hold an abrasive tip that has a surface area of abrasive particles that is the same as the surface area of the smaller abrasive tip 2001. This allows, for example, the same tip holder to be used for abrasive tips that have two different surface areas of abrasive surfaces.

Figure 21:
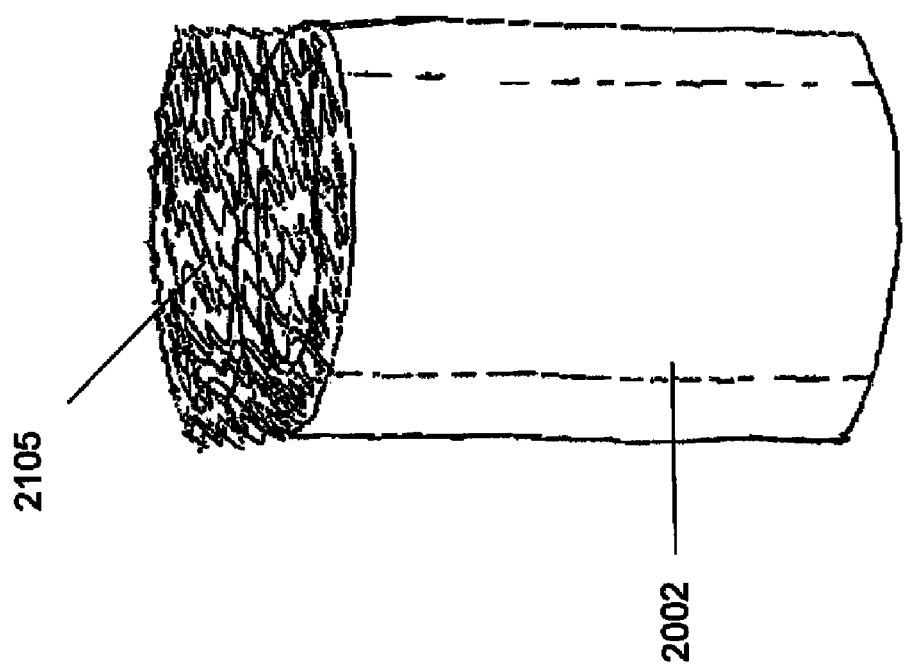
FIG. 21 shows a side view of a third implementation of an abrasive tip with an abrasive mesh having a six millimeter diameter.

FIG. 21 shows a specific implementation of an abrasive mesh tip 2105 which uses a nonwoven nylon web, such as that available from, among others, 3M Corporation. The abrasive mesh tip may be placed in the same tip holder 2002 that is used for the abrasive tip 2001. In other implementations, the tip holder will be different. The tip holder 2001 may also be integrated with the abrasive mesh tip 2105 as a single unit.

In a specific implementation, fluid flows through the center of the abrasive mesh tip 2105, around a perimeter of the abrasive mesh tip 2105, or both. The mesh separates the opening for fluid from the skin so that fluid can flow out.

Figure 22:
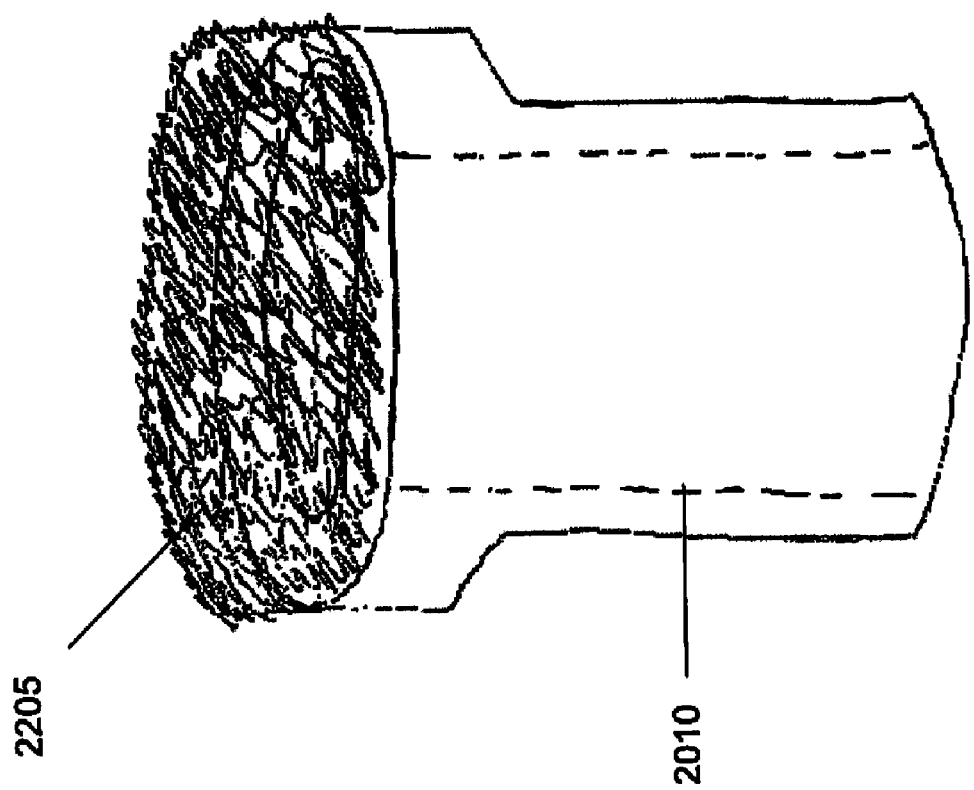
FIG. 22 shows a side view of a fourth implementation of an abrasive tip with an abrasive mesh having a nine millimeter diameter.

In a specific implementation, the abrasive mesh tip 2105 has a diameter of 6 millimeters. However, the size of the abrasive mesh tip may vary. For example, FIG. 22 shows a specific implementation of an abrasive mesh tip 2205 which has a 9 millimeter diameter.

In addition to the 6 millimeter and 9 millimeter sizes, there may be many more sizes. Where, for example, circular shaped abrasive mesh tips are used, the diameter may range from 4 millimeters to 20 millimeters. This includes, for example, less than 4 millimeters, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or more than 20 millimeters in diameter.

The height of the abrasive mesh tip may also vary greatly. The height is typically about 2 millimeters, but can range from about 0.4 millimeters to about 15 millimeters. For example, the height maybe 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 11, 12, 13, 14, or more than 15 millimeters. In other implementations, the height may be less than 0.4 millimeters.

Figure 23:
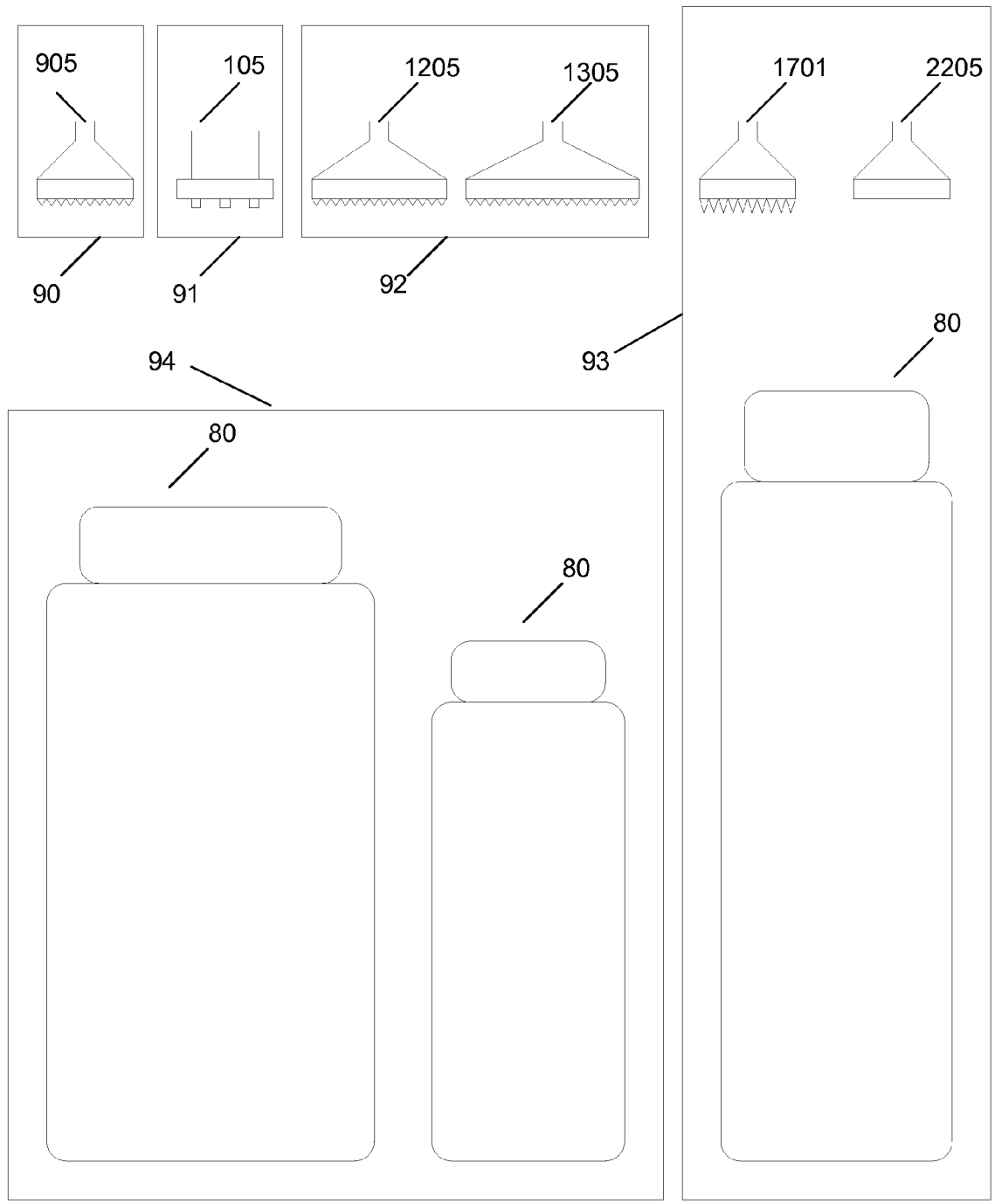
FIG. 23 shows options for packaging the abrasive tips, abrasive mesh tips, bristled tips, and bottles of fluid.

FIG. 23 shows examples of several packaging options for the tips (e.g., smooth tips, abrasive tips, abrasive mesh tips, bristled tips) and bottles of fluid.

In a specific implementation, the tips may be individually packaged 90, 91. In other implementations, the tips may be provided as a kit 92. The kit may contain identical tips, tips having different sizes, tips having different levels of abrasiveness (e.g, 100 grit, 200 grit, 300 grit) and types of abrasive elements (e.g., grit, bristle, abrasive mesh), or combinations of these. For example a kit may contain several tips with grit ranges from 100 grit to 300 grit. A microdermabrasion session may start with the most abrasive grit, such as 100 grit, in order to quickly remove large portions of skin. As the patient's skin becomes smoother, less abrasive tips may then be used to produce a smooth skin surface.

In a specific implementation, the bottles of fluid 80 may be individually packaged separate from the tips. In another implementation, multiple bottles of fluids may be packaged together 94, separate from the tips.

In yet another implementation, a single tip or multiple tips may be packaged 93 with a bottle of fluid 80 or multiple bottles of fluid. In a specific implementation, one bottle of fluid may be equivalent to one microdermabrasion session. A single tip, intended for use for one session, may then be packaged with the bottle of fluid. The tip and bottle may be packaged in a sterile container. A user may then remove the tip and bottle from its packaging in view of the patient. This allows the patient to see that a new tip is being used. It also allows the patient to see that the fluid in the bottle has not been tampered or diluted.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A microdermabrasion device comprising:
   a tip comprising an abrading surface formed on a first side;
   a collar portion on a second side of the tip, wherein the second side is opposite of the first side;
   a plurality of fluid channels formed on a second side of the tip, each channel extending through the collar through a first edge to a second edge of the tip, wherein the second edge of the tip is perpendicular to and touches the first side, and an angle between the first side and the first edge is less than ninety degrees; and
   at least one key notch, formed on the collar portion between two channel openings, wherein a surface of the collar is perpendicular to the first side,
   wherein fluid channels on the second side of the tip mate with corresponding fluid channels in a tip holder to form complete fluid channel openings.

2. The device of claim 1 wherein the first side of the tip comprises a circle shape.

3. The device of claim 1 wherein each fluid channel is a groove formed in the first edge.

4. The device of claim 1 wherein there is a split in the collar portion at each point where a fluid channel passes through the collar.

5. The device of claim 1 wherein the plurality of fluid channels are evenly distributed about the second edge.

6. The device of claim 1 wherein an angle between the fluid channels is 360 degrees divided a total number of fluid channels.

7. The device of claim 1 wherein a first fluid channel has a first end at the first edge, a second fluid channel has a second end at the first edge, and the first and second ends are opposite of each other on the first edge.

8. The device of claim 1 wherein the tip comprises four fluid channels.

9. The device of claim 1 wherein abrading surface comprises an abrasive disk coupled to the first side.

10. The device of claim 1 wherein the collar comprises at least one key notch for each channel.

11. The device of claim 1 wherein the abrading surface is planar.

12. The device of claim 1 wherein the fluid channels do not pass through the abrading surface.

13. The device of claim 1 wherein the tip is removable, and the at least one key notch aligns the tip for insertion into the microderabrasion device.

14. The device of claim 1 wherein the tip comprises four or fewer fluid channels.

15. The device of claim 1 wherein the abrading surface is planar and the collar portion extends in a direction perpendicular to the abrading surface.

16. The device of claim 1 wherein the at least one key notch extends from the collar surface in a direction away from a center axis through the tip.

17. A microdermabrasion device comprising:
   a tip comprising an abrading surface coupled to a planar tip structure formed on a first side;
   a collar portion on a second side of the tip, wherein the second side is opposite of the first side, and the collar portion extends perpendicularly to the planar tip structure;
   a plurality of fluid channels formed on a second side of the tip, each channel extending through the collar through a first edge to a second edge of the tip, wherein the second edge of the tip is perpendicular to and touches the first side, and an angle between the first side and the first edge is less than ninety degrees; and
   at least one key notch, formed on the collar portion between two channel openings, wherein a surface of the collar is perpendicular to the first side, wherein fluid channels on the second side of the tip mate with corresponding fluid channels in a tip holder to form complete fluid channel openings.

18. The device of claim 17 wherein the abrading surface comprises aluminum oxide particles.

19. The device of claim 17 wherein there is a split in the collar portion at each point where a fluid channel passes through the collar.

20. The device of claim 17 wherein the abrading surface comprises a continuous circular disk having no openings within boundaries of the disk.

21. The device of claim 17 wherein the fluid channels comprise grooves on the second side of the tip, and the grooves do not pass through the abrading surface.

22. The device of claim 17 wherein the tip is made of a polymer.

23. The device of claim 17 wherein the at least one key notch extends from the collar surface in a direction away from a center axis through the tip.

* * * * *